(12) United States Patent
Hung et al.

(10) Patent No.: US 6,573,047 B1
(45) Date of Patent: Jun. 3, 2003

(54) DETECTION OF NUCLEOTIDE SEQUENCE VARIATION THROUGH FLUORESCENCE RESONANCE ENERGY TRANSFER LABEL GENERATION

(75) Inventors: Su-Chun Hung, Mountain View, CA (US); Alexander N. Glazer, Orinda, CA (US); Richard A. Mathies, Moraga, CA (US)

(73) Assignee: DNA Sciences, Inc., Fremont, CA (US)

(*) Notice: Subject to any disclaimer, the term of this patent is extended or adjusted under 35 U.S.C. 154(b) by 0 days.

(21) Appl. No.: 09/547,292

(22) Filed: Apr. 11, 2000

Related U.S. Application Data

(60) Provisional application No. 60/129,129, filed on Apr. 13, 1999.

(51) Int. Cl.[7] .......................... C12Q 1/68; C12P 19/34; C07H 21/04
(52) U.S. Cl. .......................... 435/6; 435/7.9; 435/91.1; 435/91.2; 536/23.1; 536/23.5; 536/24.31; 536/24.33
(58) Field of Search .............................. 435/5, 6, 91.1; 536/64.33

(56) References Cited

U.S. PATENT DOCUMENTS

| | | | |
|---|---|---|---|
| 4,656,127 A | 4/1987 | Mundy | 435/6 |
| 4,863,849 A | 9/1989 | Melamede | 435/6 |
| 4,865,968 A | 9/1989 | Orgel et al. | |
| 4,962,037 A | 10/1990 | Jett et al. | 435/6 |
| 4,996,143 A * | 2/1991 | Heller et al. | 435/6 |
| 5,137,806 A | 8/1992 | LeMaistre et al. | 435/6 |
| 5,171,534 A | 12/1992 | Smith et al. | 472/82.05 |
| 5,210,015 A | 5/1993 | Gelfand et al. | 435/6 |
| 5,219,727 A | 6/1993 | Wang et al. | 435/6 |
| 5,302,509 A | 4/1994 | Cheeseman | 435/6 |
| 5,487,972 A | 1/1996 | Gelfand et al. | 435/6 |
| 5,518,900 A | 5/1996 | Nikiforov et al. | |
| 5,538,848 A | 7/1996 | Livak et al. | 435/5 |
| 5,547,839 A | 8/1996 | Dower et al. | 435/6 |
| 5,639,611 A | 6/1997 | Wallace et al. | 435/6 |
| 5,654,419 A | 8/1997 | Mathies et al. | 536/25.4 |
| 5,688,648 A | 11/1997 | Mathies et al. | 435/6 |
| 5,707,804 A | 1/1998 | Mathies et al. | 435/6 |
| 5,710,028 A | 1/1998 | Eyal et al. | 435/91.1 |
| 5,728,528 A | 3/1998 | Mathies et al. | 435/6 |
| 5,804,375 A | 9/1998 | Gelfand et al. | 435/6 |
| 5,821,058 A | 10/1998 | Smith et al. | 435/6 |
| 5,827,653 A | 10/1998 | Sammes et al. | 435/6 |
| 5,834,189 A | 11/1998 | Stevens et al. | |
| 5,846,710 A | 12/1998 | Bajaj | 435/6 |
| 5,853,992 A | 12/1998 | Glazer et al. | 435/6 |
| 5,856,092 A | 1/1999 | Dale et al. | 435/6 |
| 5,863,736 A | 1/1999 | Haaland | 435/6 |
| 5,866,336 A | 2/1999 | Nazarenko et al. | 435/6 |
| 5,876,930 A | 3/1999 | Livak et al. | 435/6 |
| 5,885,775 A | 3/1999 | Haff et al. | |
| 5,888,819 A | 3/1999 | Goelet et al. | 435/5 |
| 5,891,629 A | 4/1999 | Goldrick | |
| 5,945,283 A | 8/1999 | Kwok et al. | 435/6 |
| 5,981,186 A | 11/1999 | Gabe et al. | 435/6 |
| 6,004,744 A | 12/1999 | Goelet et al. | 435/5 |
| 6,013,431 A | 1/2000 | Suderlund et al. | 435/5 |
| 6,020,137 A * | 2/2000 | Lapidus et al. | 435/6 |
| 6,027,890 A | 2/2000 | Ness et al. | |
| 6,107,061 A | 8/2000 | Johnson | |
| 6,322,980 B1 | 11/2001 | Singh | |

FOREIGN PATENT DOCUMENTS

| | | |
|---|---|---|
| EP | 0 229 943 | 7/1987 |
| EP | 0 601 889 | 6/1994 |
| EP | 0 412 883 | 11/1996 |
| GB | 2 252 407 | 8/1992 |
| GB | 2317951 A * | 4/1998 |
| WO | WO 90/09455 | 8/1990 |
| WO | WO 90/13666 | 11/1990 |
| WO | WO 91/13075 | 9/1991 |
| WO | WO 92/15712 | 9/1992 |
| WO | WO 92/16657 | 10/1992 |
| WO | WO 93/05183 | 3/1993 |
| WO | WO 93/25563 | 12/1993 |
| WO | WO 97/22719 | 6/1997 |
| WO | WO 98/59066 | 12/1998 |

OTHER PUBLICATIONS

US 5,747,249, 5/1998, Smith et al. (withdrawn)

Ambrose, B. J. B. and Pless, R. C.; *DNA Sequencing: Chemical Methods, Methods in Enzymology*, (1987) vol. 152, pp. 522–539.

Brand, Eve et al., *Structural Analysis and Evaluation Of The Aldosterone Synthase Gene In Hypertension, Hypertension*, (1998) vol. 32, pp. 198–204.

Cardullo, R. A. et al., *Detection of Nucleic Acid Hybridization by Nonradiative Fluorescence Resonance Energy Transfer, Proc. Nat. Acad. Sci. USA*, Dec., 1988, vol. 85, pp. 8790–8794.

Chen, Xiangning and Kwok; Pui–Yan; *Homogeneous Genotyping Assays For Single Nucleotide Polymorphisms With Fluorescence Resonance Energy Transfer Detection, Genetic Analysis: Biomolecular Engineering*, (1999) vol. 14, pp. 157–163.

(List continued on next page.)

*Primary Examiner*—Kenneth R. Horlick
*Assistant Examiner*—Alexander H. Spiegler
(74) *Attorney, Agent, or Firm*—Townsend and Townsend and Crew LLP

(57) ABSTRACT

The present invention provides methods and kits for identifying nucleotides at a variant site in a target molecule by forming fluorescence resonance energy transfer labeled product. The location and type of fluorescent labels in the labeled product provide strong signals and relatively high spectral purity that facilitate detection. Utilizing various secondary labels and different combinations of acceptor and donor labels, certain methods permit multiple analyses to be conducted simultaneously and at high throughput. The methods can be used in a variety of applications such as analyzing point mutations and single nucleotide polymorphisms (SNPs). In addition, the methods have utility in other applications in which specific sequence information is of value, including detection of pathogens, paternity disputes, prenatal testing and forensic analysis.

54 Claims, 7 Drawing Sheets

OTHER PUBLICATIONS

Chen, Xiangning and Kwok, Pui–Yan; *Template–directed Dye–terminator Incorporation (TDI) Assay: A Homogeneous DNA Diagnostic Method Based On Fluorescence Resonance Energy Transfer, Nucleic Acids Research*(1997) vol. 25, No. 2, pp. 347–353.

Chen, Xiangning et al., *A Homogeneous, Ligase–Mediated DNA Diagnostic Test, Genome Research* (1998) vol. 8, pp. 549–556.

Chen, Xiangning et al., *Fluorescence Energy Transfer Detection As A Homogeneous DNA Diagnostic Method, Proc. Natl. Acad. Sci. USA*, Sep., 1997, vol. 94, pp. 10756–10761.

Glazer, Alexander N. and Mathies, Richard A., *Energy–Transfer Fluorescent Reagents For DNA Analyses, Analytical Biotechnology*, (1997) vol. 8, No. 1, pp. 94–102.

Hung, Su–Chun et al., *Cyanine Dyes With High Absorption Cross Section As Donar Chromophores In Energy Transfer Primers, Analytical Biochemistry*(1996) vol. 243, pp. 15–27.

Hung, Su–Chun et al., *Optimization Of Spectroscopic And Electrophoretic Properties Of Energy Transfer Primers, Analytical Biochemistry*, (1997) vol. 252, pp. 78–88.

Hung, Su–Chun et al., *Comparison Of Fluorescence Energy Transfer Primers, Analytical Biochemistry*, (1998) vol. 255, pp. 32–38.

Innis, Michael A. et al., *DNA Sequencing With Thermus Aquaticus DNA Polymerase And Direct Sequencing Of Polymerase Chain Reaction–Amplified DNA, Proc. Natl. Acad. Sci. USA*, Dec., 1988, vol. 85, pp. 9436–9440.

Ju, Jingyue et al., *Energy Transfer Primers: A New Fluorescence Labeling Paradigm For DNA Sequencing And Analysis, Nature Medicine* Feb., 1996, vol. 2, No. 2, pp. 246–249.

Ju, Jingyue, et al., *Cassette Labeling For Facile Construction Of Energy Transfer Fluorescent Primers, Nucleic Acids Research*, (1996) vol. 24, No. 6, pp. 1144–1148.

Ju, Jingyue et al., *Design and Synthesis of Fluorescence Energy Transfer Dye–Labeled Primers and Their Application for DNA Sequencing and Analysis, Analytical Biochemistry*, (1995) vol. 231, pp. 131–140.

Lee, Linda G.; Connell, Charles R. and Bloch, Will; *Allelic Discrimination By Nick–translation PCR With Fluorogenic Probes, Nucleic Acids Research*, (1993) vol. 21, No. 16, pp. 3761–3766.

Levedakou Eleni, N.; Landegren, Ulf and Hood, Leroy E.; *A Strategy To Study Gene Polymorphism By Direct Sequence Analysis Of Cosmid Clones And Amplified Genomic DNA, BioTechniques*, (1989) vol. 7, No. 5, pp. 438–442.

Mead, D. A. et al., *Bst DNA Polymerase Permits Rapid Sequence Analysis From Nanogram Amounts Of Template, BioTechniques*, (1991) vol. 11, No. 1, pp. 76–87.

Prober, James M. et al., *A System For Rapid DNA Sequencing With Fluorescent Chain–Terminating Dideoxynucleotides, Science*, Oct. 16, 1987, vol. 238, pp. 336–341.

Risch, Neil and Merikangas, Kathleen; *The Future Of Genetic Studies Of Complex Human Diseases, Science*, Sep. 13, 1996, vol. 273, pp. 1516–1517.

Sanger, F., Nicklen, S. and Coulson, A. R.; *DNA Sequencing With Chain–Terminating Inhibitors, Proc. Natl. Acad. Sci. USA*, Dec., 1977, vol. 74, No. 12, pp. 5463–5467.

Wang, Yiwen et al., *Microsatellite–based Cancer Detection Using Capillary Array Electrophoresis And Energy–transfer Fluorescent Primers, Electrophoresis*(1997) vol. 18, pp. 1742–1749.

Wegmuller, B.; Luthy, J. and Candrian, U.; *3'–5' Proofreading–Induced Detection Of Point Mutations By PCR Using Tli DNA Polymerase, Nucleic Acids Research*, (1995) vol. 23, No. 2, pp. 311–312.

Yu, Hongrun et al., *Identification Of Human Plasma Kallikrein Gene Polymorphisms and Evaluation Of Their Role In End–Stage Renal Disease, Hypertension* (1998) vol. 31, pp. 906–911.

Ahern, Holly; Biochemical, Reagent Kits Offer Scientists Good Return on Investment, http://www.the–scientist.library.upenn.edu/yr1995/july/tools_950724.html.

Ausubel, F.M.; Polyacrylamide Gel Electrophoresis, Current Protocols in Molecular Biology; John Wiley & Sons (1988), pp. 6.3–8, 6.36–6.38.

Livak, Kenneth J.; Allelic discrimination using fluorogenic probes and the 5' nuclease assay; Genetic Analysis: Biomolecular Engineering; 1999; pp. 143–149.

Piggee, Christine A. et al.; Capillary electrophoresis for the detection of known point mutations by single–nucleotide primer extension and laser–induced fluorescence detection; Journal of Chromatography A; 1997; pp. 367–375.

Wu, Dan Y. et al.; Allele–specific enzymatic amplification of β–globin genomic DNA for diagnosis of sickle cell anemia; PNAS USA; Apr. 1989; vol. 86; pp. 2757–2760.

Singer, Maxine and Paul Berg; Genes & Genomes a changing perspective; p. 245; 1991; University Science Books.

* cited by examiner

D:

CYA

T*:

AminoModifier C6dT

N:

Uni-Link AminoModifier

DETECTION OF NUCLEOTIDE SEQUENCE VARIATION THROUGH FLUORESCENCE RESONANCE ENERGY TRANSFER LABEL GENERATION

CROSS-REFERENCES TO RELATED APPLICATIONS

This application claims the benefit of U.S. Provisional Application No. 60/129,129, filed Apr. 13, 1999, which is incorporated by reference herein in its entirety for all purposes.

FIELD OF THE INVENTION

This invention relates to the field of molecular genetics, particularly the identification and detection of certain nucleotide sequences.

BACKGROUND OF THE INVENTION

Familial clustering of common disorders independent of known risk factors indicates that genetic epidemiology studies may provide important leads to understanding the pathogenesis of many complex diseases and help identify individuals at increased risk. The multifactorial nature of many complex diseases suggests that numerous genes, each with multiple alleles having small to moderate effects, may account for the majority of genetic variation involved in defining risk of common chronic diseases on a population basis. Nucleotide variations that are found in at least one percent of the populations are called single nucleotide polymorphisms, or simply SNPs. SNPs occur in roughly one of every 500 bases. Consequently, some 200,000 SNPs lie within coding regions of genes. Much of the genetic variation between individual humans that contributes to differences in susceptibility to disease is believed to reflect SNP variations in DNA (Risch and Merikangas, 1996). Some SNPs cause or strongly contribute to specific diseases. For example, sickle cell anemia is caused solely by the change of an A to a T in the gene encoding the β-chain of hemoglobin. There are many reports of positive association of SNPs with complex diseases such as hypertension (Brand et al., 1998), or end-stage renal disease (Yu et al., 1998).

SNPs may also prove to be useful in pharmacogenomics, a new approach to drug design, testing and utilization. Here, the premise is that depending on their genetic makeup, individuals respond differently to particular drugs. On another front, the use of SNPs as biallelic genetic markers offers the promise of rapid, highly automated genotyping.

In existing SNP assays, PCR primers flanking each SNP locus to be interrogated are chosen from publicly available genomic sequence information. In one format, the forward PCR primers are designed such that the nucleotide at the 3'-end of the primer complements the base adjacent to the SNP site. The regions containing the SNP polymorphism are then amplified by PCR and the resulting products are purified prior to a primer extension reaction. The extension reaction uses each PCR product as template and fluorescent dye-labeled dideoxynucleotide triphosphates (ca. 100-fold excess) to identify the base present at each SNP site, i.e., the SNP alleles. Each primer extension experiment requires pair(s) of dye-labeled ddNTPs (e.g., R110-ddTTP and ROX-ddCTP for an A-to-G nucleotide change). The labeled extension products representing the SNP alleles are separated by capillary electrophoresis and detected by laser-induced fluorescence.

Various aspects of existing methods limit their efficacy in analyzing SNPs. For example, some of the following commercially available reagents are used in current SNP assays. Rhodamine dye-labeled terminators are available in 16 dye/base combinations from E.I. DuPont de Nemours & Co. ET-labeled terminators (i.e., Energy-Transfer-labeled terminators) can be purchased from Applied Biosystems (BigDye terminator premix kit), or from Amersham Pharmacia Biotech (DYEnamic ET terminator premix kit). A disadvantage of using the ET-labeled terminators is that they offer no flexibility in the choice of dye/base combinations. Only one set of four ET-labeled terminators is available with a particular ET-label on each base. Moreover, both BigDye and DYEnamic ET terminators use FAM derivatives as donors that provide relatively low signal strengths and spectral purity. Finally, these ET-labeled terminators are not readily available other than as components of kits.

Other problems associated with current SNP assays are as follows: 1) With excitation at one wavelength, single dye-labeled terminators give lower signal intensities than ET-labeled terminators; 2) both single dye-labeled and ET-labeled terminator assays provide no discrimination between the fluorescence emission of the extended target and of the reagents; 3) assays using ET-labeled primers likewise provide no fluorescence emission discrimination between extended and unextended primer; 4) purification is required to remove the large excess of unincorporated labeled-ddNTPs (or labeled primers) to avoid masking of the extended target peak. For research studies, such a purification step can be tolerated, but it needs to be eliminated in high throughput assays.

A template-directed dye-terminator incorporation (TDI) assay, a homogeneous DNA diagnostic solution assay based on fluorescence resonance energy transfer (FRET), has recently been developed. In this assay, amplified genomic DNA fragments containing polymorphic sites are incubated with a 5'-FAM-labeled primer in the presence of allelic acceptor dye-labeled dideoxy terminators (Chen and Kwok, 1997a,b). The FAM-labeled primer is extended one base by the acceptor-labeled terminator specific for the allele present on the template. The reaction mixture is then analyzed for changes in fluorescence intensities without separation. This method detects the intramolecular FRET against a background of intermolecular FRET. A related dye-labeled oligonucleotide ligation (DOL) assay in which a donor dye-labeled common probe is joined to an allele-specific, acceptor dye-labeled probe by DNA ligase has also been developed (Chen and Kwok, 1998, 1999).

There are certain limitations associated with the TDI assay. First, in some instances only an overall fluorescence emission is measured, thus, no multiplexing of SNPs can be performed. Second, the efficiency of FRET is sensitive to the distance between the donor and acceptor in ET primers (Ju et al., 1995; Hung et al. 1997). The primers used in the TDI assay carry the donor dye (FAM) at the 5'-end. Moreover, the primer lengths typically are more than 18 nucleotides long. Therefore, the ET-labeled SNP products are formed with donor-acceptor dye pairs separated by more than 18 bases. This long spacing results in poor ET efficiency and requires that the extended primer be dissociated from the template before detection can occur. Also, with FAM as a donor, the residual donor fluorescence emission is relatively high. Third, this assay involves either awkward calculations that create variant thresholds for different loci (Chen and Kwok, 1997a), or awkward real-time fluorescence detection for each cycle during the primer extension (Chen and Kwok, 1997b). These are not suitable for high throughput assays.

SUMMARY OF THE INVENTION

The present invention provides a variety of methods for analyzing target nucleic acids having a variant site. The invention also provides kits for performing such methods within research, clinical and laboratory settings. The methods generally involve conducting template-dependent primer extension reactions to form an energy transfer labeled extension product if a non-extendible nucleotide provided in the extension reaction mixture is complementary to the nucleotide at the variant site. The extension product includes a donor and acceptor fluorophore that together form a pair. One member of the pair is borne by the primer and the other member by the non-extendible nucleotide. By controlling various parameters such as the position of the fluorophore on the primer and the type of fluorophores utilized, certain methods of the invention can enhance signal strength and purity. Further, certain methods can be performed without the need to dissociate extension product from the target nucleic acid, or to separate other reaction components from the extension product, prior to detection.

More specifically, certain methods for analyzing variant sites in nucleic acids of interest involve hybridizing a primer bearing a first fluorophore to a segment of the target nucleic acid to form a labeled hybrid, wherein the 3'-end of the primer hybridizes to the target nucleic acid immediately adjacent to the variant site. Template-dependent extension of the primer is conducted in the presence of a polymerase and at least one non-extendible nucleotide bearing a second fluorophore, whereby a double-labeled extension product is formed if the non-extendible nucleotide is complementary to the nucleotide at the variant site and the first and second fluorophore borne by the extension product are brought into an energy transfer relationship. The first and second fluorophore borne by the primer and non-extendible nucleotide comprise a donor and an acceptor fluorophore. The presence or absence of the double-labeled extension product is then detected, the presence or absence of double-labeled extension product indicating the identity of the nucleotide at the variant site.

Because the label on the primer is located so that the fluorophores borne by the primer and the non-extendible nucleotide are brought into an energy transfer relationship during the extension reaction, the extension product can be detected while it is still hybridized to the target nucleic acid. Presence of extension product can be detected by an increase in the emission associated with the acceptor fluorophore or a decrease in emission from donor fluorophore. Other analytical methods utilize primers including modified nucleotides or nucleotide subsitutes to incorporate a fluorophore into a desired position in the primer to facilitate energy transfer once labeled non-extendible nucleotide is incorporated into the primer.

Other methods utilize particular combinations of dyes to increase signal strength while minimizing background signal from unreacted components of the extension reaction. For example, in some methods, one member of the fluorophore pair is a donor that has a high extinction coefficient and a low fluorescent quantum yield. Such a fluorophore can be paired with an acceptor fluorophore that does not exhibit strong fluorescence emissions when excited at the wavelength used to excite the donor fluorophore. Examples of such combinations include cyanine dyes as a donor (e.g., CYA, Cy2, Cy3, Cy3.5, Cy5, Cy5.5, Cy7, and Cy7.5) and rhodamine dyes as acceptor (e.g., R110, R6G, TAMRA, ROX, FAM, JOE, ZOE, TET, HEX, NAN, Texas Red, and Rhodamine Red).

The invention further provides methods for analyzing mutiple variant sites at the same time. Certain multiplexing methods comprise conducting a plurality of template-dependent extension reactions with different primers, wherein different primers hybridize adjacent different variant sites on target nucleic acids. Each extension reaction comprises: (i) hybridizing one of the different primers to a segment of a target nucleic acid, wherein the primer bears a first fluorophore and an optional secondary label and the 3'-end of the primer hybridizes to a target nucleic acid immediately adjacent to a variant site, (ii) contacting the primer with a polymerase and at least one non-extendible nucleotide bearing a second fluorophore, whereby a multi-labeled extension product is formed if the non-extendible nucleotide is complementary to the nucleotide at the variant site and the first and second fluorophore borne by the extension product are brought into an energy transfer relationship. The different primers bear different first labels and/or mass labels and different non-extendible nucleotides optionally bear different second fluorophores so that different extension products corresponding to different variant sites bear different pairs of fluorophores and/or different secondary labels. Following extension product formation, the presence or absence of the different extension products is detected. The fluorophore pair and/or secondary label borne by the extension product serves as an indicator of the identity the nucleotides at the variant sites. Extension products generated from different variant sites can be encoded by attaching different secondary labels to different primers for different extension reactions and/or differentially labeling the non-extendible nucleotides.

BRIEF DESCRIPTION OF THE DRAWINGS

FIG. 3A shows the donor cyanine dye attached within the primer sequence through either a modified thymidine (T*) or a substituted amino linker (N). FIGS. 3B and 3C depict synthetic schemes for the introduction of the donor (CYA) chromophore to primers.

DETAILED DESCRIPTION

I. ABBREVIATIONS

Figure 1A:
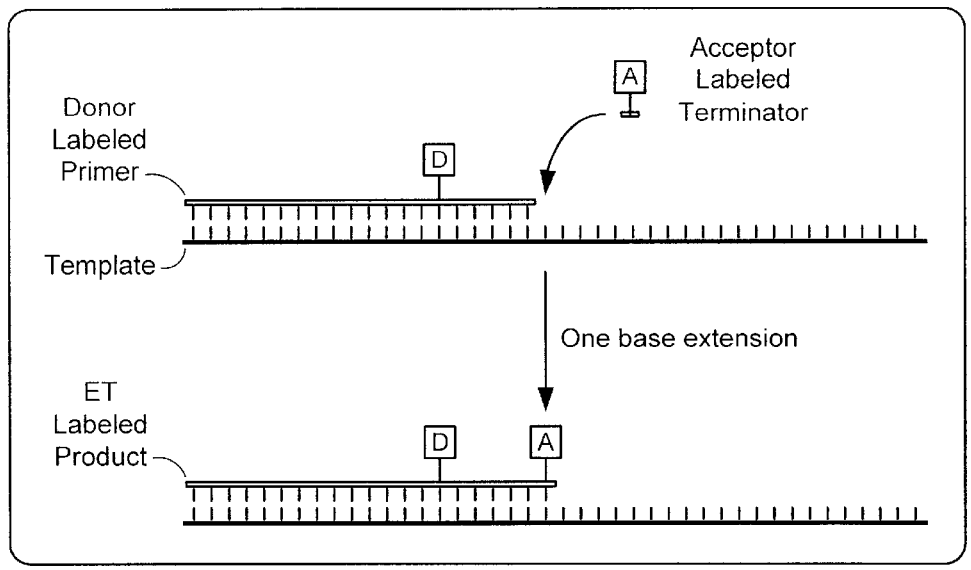
FIGS. 1A and 1B depict the formation of ET-labeled products during primer extension reactions according to certain methods of the invention. Two alternative constructs can be used: i) the donor dye (D) is placed on the primer and the acceptor dye (A) is placed on the terminator (FIG. 1A), and ii) the acceptor dye (A) is placed on the primer and the donor dye (D) is placed on the terminator (FIG. 1B).

SNP, single nucleotide polymorphism; ET, energy transfer; FRET, fluorescence resonance energy transfer; ddNTPs, dideoxyribonucleoside triphosphates; PCR, polymerase chain reaction; CYA, 3-(ε-carboxypentyl)-3'-ethyl-5,5'-dimethyloxacarbocyanine; R110, 5&6-carboxyrhodamine-110; R6G, 6-carboxyrhodamine-6G; TAMRA, N,N,N',N'-tetramethyl-6-carboxyrhodamine; ROX, 6-carboxy-X-rhodamine; FAM, 6-carboxyfluorescein; JOE, 6-carboxy-4',5'-dichloro-2',7'-dimethoxyfluorescein; HEX, 6-carboxy-2',4,4',5',7,7'-hexachlorofluorescein; TET, 6-carboxy-2',4,7,7'-tetrachlorofluorescein; ZOE, 5-carboxy-2',4',5',7'-tetrachlorofluorescein; TDI, template-directed dye-terminator incorporation; DOL, dye-labeled oligonucleotide ligation.

II. DEFINITIONS

A "nucleic acid" is a deoxyribonucleotide or ribonucleotide polymer in either single- or double-stranded form, including known analogs of natural nucleotides unless otherwise indicated.

A "polynucleotide" refers to a single- or double-stranded polymer of deoxyribonucleotide or ribonucleotide bases.

An "oligonucleotide" is a single-stranded nucleic acid ranging in length from 2 to about 500 bases. Oligonucleotides are often synthetic but can also be produced from naturally occurring polynucleotides. Oligonucleotides can be prepared by any suitable method, including, for example, cloning and restriction of appropriate sequences and direct chemical synthesis by a method such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetrahedron Lett.* 22:1859–1862 (1981); and the solid support method of U.S. Pat. No. 4,458,066.

A "primer" is a single-stranded oligonucleotide capable of acting as a point of initiation of template-directed DNA synthesis under appropriate conditions (e.g., in the presence of one or more nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides, although longer and shorter primers can be used. Short primer molecules generally require cooler temperatures to form sufficiently stable hybrid complexes with the template. A primer need not reflect the exact sequence of the template but must be sufficiently complementary to selectively hybridize with a template. The term "primer site" refers to the segment of the target nucleic acid to which a primer hybridizes. The term "primer pair" means a set of primers including a 5' "upstream primer" that hybridizes with the 5' end of the DNA sequence to be amplified and a 3' "downstream primer" that hybridizes with the complement of the 3' end of the sequence to be amplified. When reference is made to a primer hybridizing adjacent to a nucleotide site, it is meant that the primer preferably hybridizes immediately next to, or optionally within about 3 to 10 nucleotides from the site.

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary.

The term "substantially complementary" means that a primer is not perfectly complementary to its target sequence; instead, the primer is only sufficiently complementary to hybridize selectively to its respective strand at the desired primer binding site.

A "site of variation" or "variant site" when used with reference to a nucleic acid broadly refers to a site wherein the identity of nucleotide at the site varies between nucleic acids that otherwise have similar sequences. For double-stranded nucleic acids, the variant site includes the variable nucleotide on one strand and the complementary nucleotide on the other strand. A variant site can be the site of a single nucleotide polymorphism or the site of a somatic mutation, for example.

A "polymorphic marker" or "polymorphic site" is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "naturally occurring" as applied to an object means that the object can be found in nature.

The term "subject" and "individual" are used interchangeably herein to refer to any type of organism, including humans.

III. OVERVIEW

The present invention provides a variety of methods, compositions and kits for determining the identity of a nucleotide present at a variant site in a target nucleic acid. Certain methods of the invention, which the current inventors call "in situ energy transfer (ET) labeling methods," involve the template-dependent extension of a primer to generate a fluorescence energy transfer label. The methods of the present invention are designed to enhance detection and increase sample throughput.

Figure 1B:
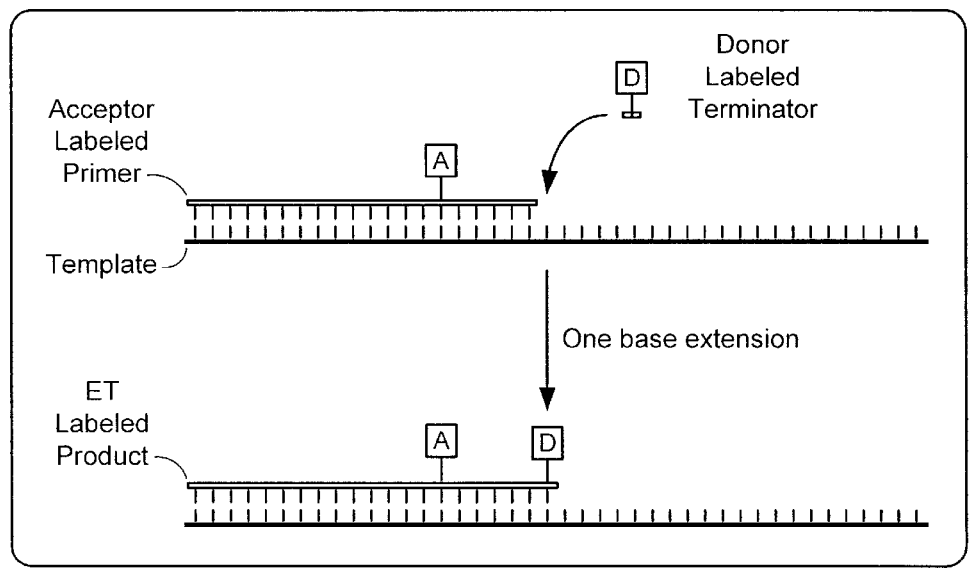

Such methods utilize a primer labeled with a donor fluorophore (D) and one or more non-extendible nucleotides (also called terminators) labeled with an acceptor fluorophore, or vice versa (see FIGS. 1A and 1B). During template extension, labeled primer incorporates a labeled non-extendible nucleotide at its 3'-end such that the donor and acceptor fluorophore are brought into an energy transfer relationship, thus forming an energy transfer-labeled extension product (ET-labeled product).

Thus, in certain methods, the location at which the primer is labeled is selected so that once a labeled non-extendible nucleotide is added to the primer, the spacing between the two fluorophores allows energy transfer to occur. Hence, with such methods, energy transfer occurs upon primer extension (i.e., addition of labeled non-extendible nucleotide), while the extension product is still hybridized to the target nucleic acid (i.e., the template). This contrasts with other methods in which donor and acceptor are so widely spaced apart during extension that energy transfer can not occur until the extension product is denatured from the target nucleic acid (i.e., the template). Only then do the donor and acceptor labels come in sufficiently close range for energy transfer to occur.

In some instances, the desired spacing is achieved by conducting methods with labeled primers wherein the fluorophore label is attached at an internal location within the primer (i.e., a nucleotide other than the nucleotides at the 3' or 5' end). Such internal labeling can be accomplished using modified nucleotides (e.g., modified thymidine (T*)) or any of a variety of nucleotide substitutes (N) such as universal linkers (e.g., Uni-Link AminoModifier). Typically, these modified nucleotides or substitutes include an amino functionality that is available for fluorophore attachment (see FIGS. 2B and 2C. SNP genotyping using CYA-labeled primers can be performed with each of these two modifiers (see FIGS. 3A–3C).

Certain methods utilize selected donor fluorophores (e.g., cyanine dyes such as CYA) that have a low fluorescence quantum yield in combination with acceptors that do not exhibit strong fluorescence emissions at the excitation wavelength of the donor dye (e.g., rhodamine acceptor fluorophores that do not exhibit strong emissions at 488 nm). With such methods, signals from unincorporated primer and non-extendible nucleotides can be tolerated. Certain methods using this dye combination can provide data of high spectral purity, with clear color discrimination between products and reagents. Consequently, in some methods, the methods can be conducted in a homogenous format in which a post-extension purification step is unnecessary.

Figure 6A:
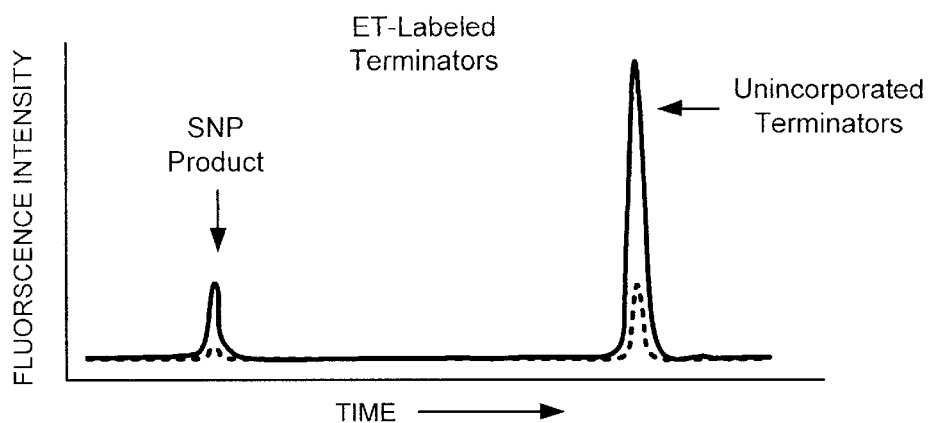
FIGS. 6A–6C show comparisons of expected signal strengths and data qualities of three different electrophoretic SNP assays using: (1) BigDye or DYEnamic ET-labeled terminators (FAM/ROX) (FIG. 6A); (2) CYA-labeled primer and ROX-labeled terminator as used in certain methods of the present invention (FIG. 6B); and (3) ROX-labeled terminator (FIG. 6C). These data are calculated for 488-nm excitation. Signals are detected in two channels: blue (505–530 nm) and red (>590 nm).
Figure 6B:
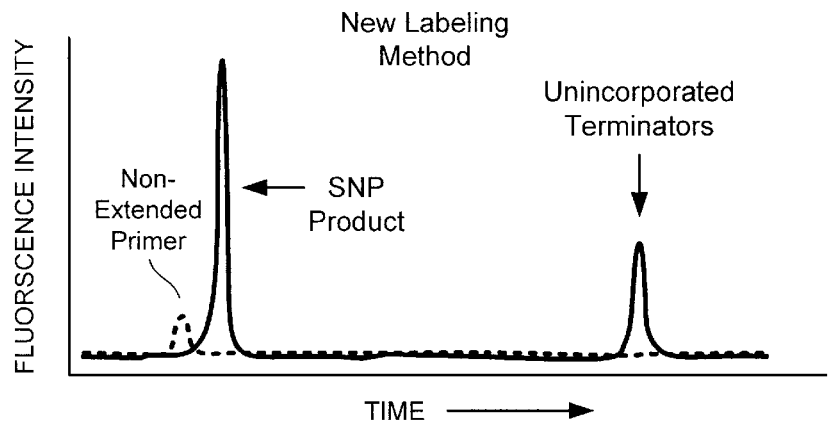
Figure 6C:
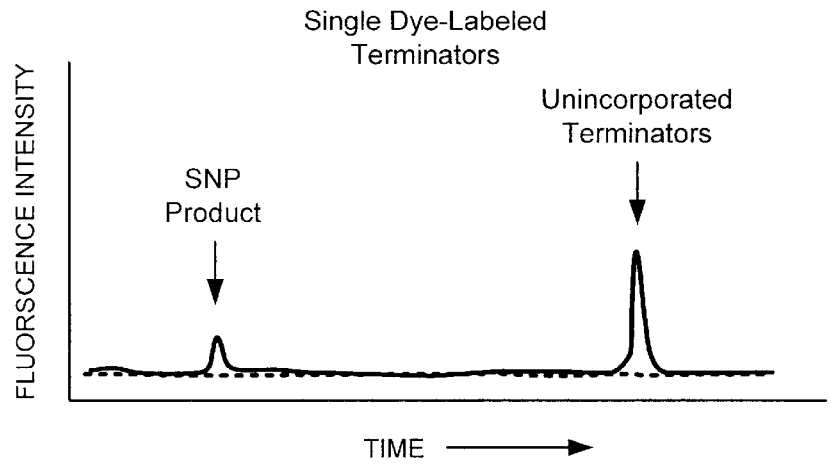

FIGS. 6A–6C show comparisons for results expected for analyses run in different formats. In FIG. 6A, reactions are run with ET-terminators such as BigDye or DYEnamic ET-labeled terminators, available from Applied Biosystems and Amersham Pharmacia Biotech, respectively. In these dyes, the donor and acceptor fluorophore are only separated by a limited number of atoms and are susceptible to quenching problems. Consequently, signal strength suffers. FIG. 6C shows signals when reactions are run with only a single fluorophore. FIG. 6B shows results when reactions are run according to methods of the present invention.

IV. DETERMINATION OF NUCLEOTIDE AT VARIANT SITE

A. General Description

Certain methods of the invention include detecting the presence of a target nucleic acid having a particular variant site or identifying which nucleotide occupies a variant site of a target nucleic acid of interest. As used herein, the term "target nucleic" acid refers to a nucleic acid that includes the variant site of interest. The target nucleic acid serves as a template during the extension reactions.

As shown in FIGS. 1A and 1B, the variant site is analyzed by conducting template-dependent extension reactions with a primer labeled with a first fluorophore and a non-extendible nucleotide (or terminator) labeled with a second fluorophore. The "non-extendible nucleotide" is a nucleotide analog which once incorporated into a primer cannot be extended further, i.e., another nucleotide cannot be attached to the 3' hydroxyl group of the non-extendible nucleotide. Thus, suitable non-extendible nucleotides include nucleotides in which the 3' hydroxyl group is substituted with a different moiety such that another nucleotide cannot be joined to the non-extendible nucleotide once incorporated into a primer. Such moieties include, but are not limited to, —H, —SH and other substituent groups. Specific examples of non-extendible nucleotides include dideoxynucleotides and arabinoside triphosphates.

Of the two fluorophores on the primer and the non-extendible nucleotide, one is a donor fluorophore and the other an acceptor fluorophore. The fluorophores are chosen so that the emission spectrum of one fluorophore (i.e., the donor fluorophore) overlaps the excitation spectrum of the other fluorophore (i.e., the acceptor fluorophore), such a donor and acceptor constituting a donor/acceptor pair. In some instances, the primer bears the donor fluorophore and the non-extendible nucleotide bears the acceptor fluorophore (FIG. 1A) of the donor/acceptor pair; whereas in other methods, the primer bears the acceptor fluorophore and the non-extendible nucleotide the donor fluorophore (FIG. 1B).

During the extension reaction, a labeled primer complementary to a target nucleic acid anneals to the target nucleic acid such that the 3'-end of the primer hybridizes adjacent to, but does not span, a variant site located within the target nucleic acid. The extension reaction is conducted in the presence of one or more labeled non-extendible nucleotides. If the reaction mixture includes a non-extendible nucleotide that is complementary to the nucleotide present at the variant site of the target nucleic acid, then the complementary nucleotide is added to the 3'-end of the primer to generate an energy transfer (ET) labeled extension product bearing both a donor and acceptor fluorophore of a donor/acceptor pair (FIGS. 1A and 1B). The addition of the non-extendible nucleotide brings the donor and acceptor within sufficiently close contact to one another such that energy transfer between the two fluorophores can occur.

The presence or absence of energy transfer labeled extension products are then detected. In some instances, detection can be performed without having to denature or separate the extension product from the target nucleic acid. Energy transfer between fluorophores can be detected either as an increase in the fluorescence emission by the acceptor fluorophore or as a decrease in the fluorescence emission of the donor fluorophore. Since the non-extendible nucleotide incorporated into the extension product is complementary to the nucleotide at the variant site, the identity of the incorporated non-extendible nucleotide is an indictor of the nucleotide occupying the variant site.

B. Primer Hybridization

1. Denaturation/Strand Separation

Figure 4:
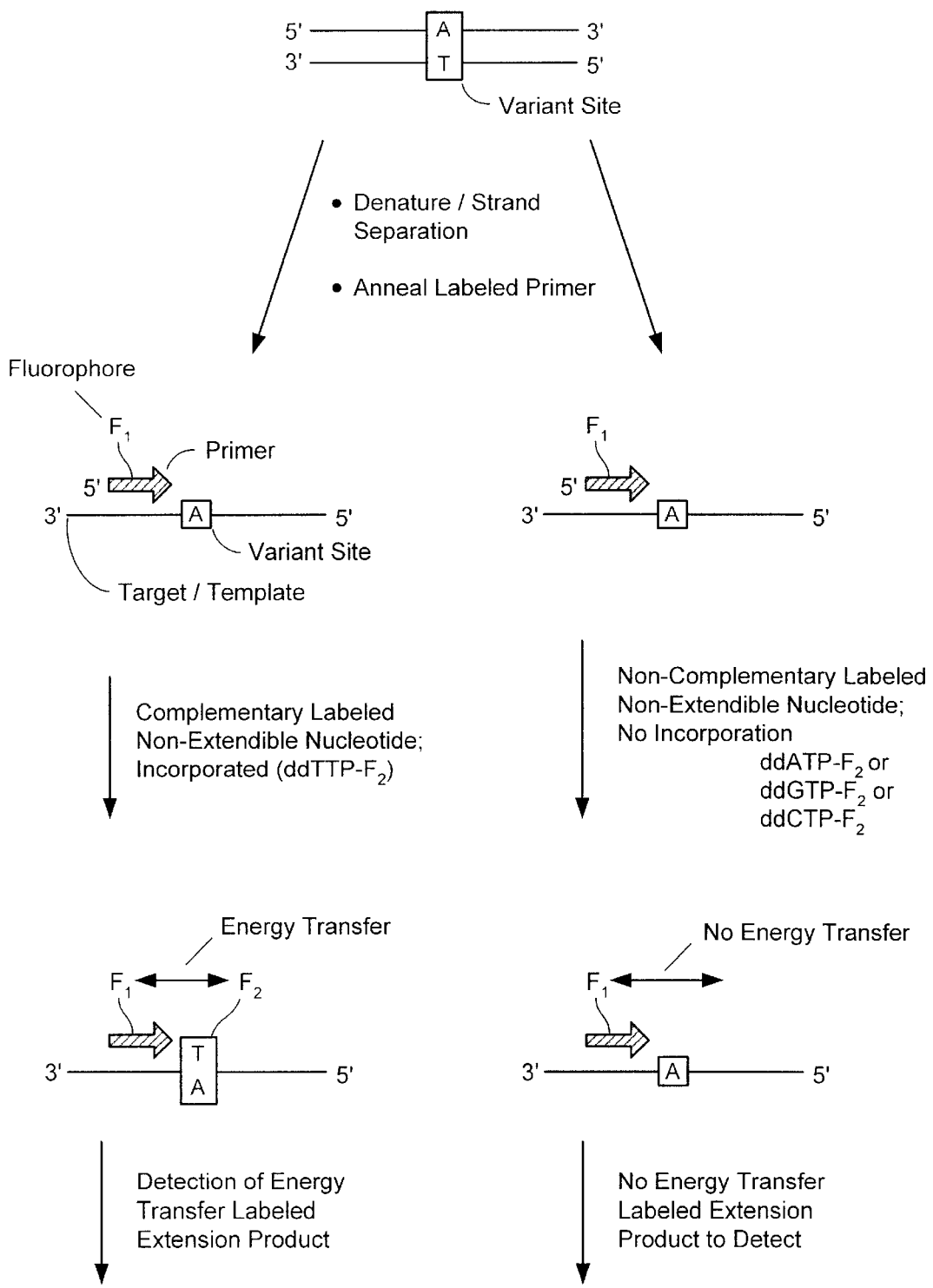
FIG. 4 summarizes certain steps in certain analytical methods of the invention.

The various major steps of certain methods of the invention are illustrated in FIG. 4. It will be appreciated by those with skill in the art that the identity of the nucleotides represented at the variant site in FIG. 4 have been arbitrarily selected and that the nucleotides at the variant site could be any of the standard four bases (i.e., A, T, G or C). The particular variant site shown if FIG. 4 is for an A polymorphic form.

In some instances, the methods of the invention begin with amplification of the target nucleic acid. Amplification of the target nucleic acid is according to established methods and is described further in the section on sample preparation supra. If the sample includes duplex target nucleic acid, the double-stranded nucleic acid is treated to obtain unpaired nucleotides that at least span the variant site of interest or, alternatively, to obtain separate strands. Of course, if the target nucleic acid is already single-stranded, such a step is unnecessary. Strand separation can be achieved using various denaturing conditions that are known in the art including, for example, heat, alkali, formamide, urea, glyoxal and combinations thereof. Typically, strand separation is achieved using heat denaturation at temperatures ranging from 80° C. to about 105° C. for time periods ranging from about 1 to 10 minutes.

2. Annealing

A primer is then annealed under hybridizing conditions to a template strand of the target nucleic acid. The primer is capable of specifically hybridizing to a segment of the target nucleic acid such that its 3'-end is adjacent to the variant site on the target nucleic acid (see FIG. 4). As used herein, the term "adjacent" when used in reference to hybridization between the primer and target nucleic acid typically means that the primer hybridizes to the target nucleic acid so that its 3'-end is immediately 5' to the variant site. However, the 3'-end can be located several nucleotides 5' to the variant site so long as none of the nucleotides between the 3'-end of the primer and the variant site are the same as a nucleotide that potentially occupies the variant site. In such instances, the 3'-end of the primer is typically within 3 to 10 nucleotides from the variant site. In such an instance, unlabeled deoxynulceoside triphosphates (dNTPs) complementary to the nucleotides between the 3' primer end and the variant site should also be included in the extension reaction mixture.

The primer is labeled with a fluorophore, which can be either a donor or an acceptor fluorophore. The fluorophore can be located at any position of the primer sequence so long as the fluorophore does not interfere with incorporation of the non-extendible nucleotide at the 3'-end of the primer such that formation of ET-labeled extension product falls below the detection limit of the detector. The fluorophore is also positioned so that once the non-extendible nucleotide is incorporated the donor and acceptor fluorophores are within an energy transfer relationship. In general, however, the primer fluorophore can be located at the 5'-end, the 3'-end, or at an internal location therebetween. Primers can be labeled internally at nucleotides, modified nucleotides or nucleotide substitutes as described more fully in the section on primers. In certain methods (e.g., multiplexing), the primer also bears a secondary label. Such labels can be used to identify which sample a primer corresponds with when extension products from different reactions are pooled prior to detection (see infra).

As used herein, the term "energy transfer relationship" means that the distance separating the donor and acceptor fluorophore is such that once the donor fluorophore is excited it can transfer energy to the acceptor fluorophore, such that a detectable change in the emission characteristics of either the donor and/or acceptor occurs. Generally the primer fluorophore is positioned so as to give a donor-acceptor spacing of 1–20 nucleotides, in other instances, 3–10 nucleotides, and, in still other instances, 4–6 nucleotides. As used herein the term "donor-acceptor spacing" or simply "spacing" between donor and acceptor refers to the number of nucleotides between the two fluorophores, without counting the modified nucleotide or substitute that bears the donor or acceptor.

C. Primer Extension

The non-extendible nucleotides to be incorporated at the 3'-end of the primer can be provided according to a variety of different formats. In general, one to four labeled non-extendible nucleotides can be added to an extension reaction mixture. If more than a single non-extendible nucleotide is added, typically different types of non-extendible nucleotides bear different labels. Factors influencing the choice of how may non-extendible nucleotides to include in the reaction mixture are discussed infra in the sections on genotyping and multiplexing.

A polymerase is also added to each reaction mixture to initiate the incorporation of one or more of the labeled non-extendible nucleotides (FIG. 4). If an added non-extendible nucleotide is complementary to the nucleotide at the variant site of the target nucleic acid, then the polymerase catalyzes the incorporation of the complementary non-extendible nucleotide to generate an ET-labeled extension product in which the donor and acceptor fluorophores are brought into an energy transfer relationship. If, however, the non-extendible nucleotide(s) present in the reaction mixture is(are) not complementary to the nucleotide occupying the variant site, then ET-labeled extension product is not formed (FIG. 4). Since the incorporated non-extendible nucleotide is complementary to the nucleotide occupying the variant site, the incorporated nucleotide provides the basis for identifying the nucleotide(s) at the site of variation.

A variety of different polymerases can be used, including both thermostable and non-thermostable polymerases. Suitable polymerases include, for example, DNA polymerases of several types so long as the polymerase is primer and template-dependent. Specific examples include *E. coli* DNA polymerase I or the "Klenow fragment" thereof, T4 DNA polymerase, T7 DNA polymerase ("Sequenase"), *T. acuanticus* DNA polymerase, *T. thermophilus* polymerase, or a retroviral reverse transcriptase. RNA polymerases such as T3 or T7 RNA polymerase can also be used in some protocols.

D. Detection

1. Non-homogeneous Assays

In some instances, once extension reactions have been completed, ET-labeled extension product is separated from unextended primers and unincorporated non-extendible nucleotide to facilitate detection of fluorescence emission from the extension product(s). Following separation of potentially interfering components, extended primer is analyzed to detect the presence or absence of ET-labeled extension product. In certain multiplexing methods, for example, the presence of secondary label borne by the extension product is detected to distinguish which sample the extension product corresponds with (see infra).

Certain methods accomplish separation of extension product from other reaction components using size separation based techniques. Such separations can include, but are not limited to, gel electrophoresis and various chromatographic methods capable of fractionating sample components according to size (e.g., high performance liquid chromatography (HPLC) methods using a sizing column).

In some methods, the separation of extension product from other components of the reaction mixtures and the actual detection of labeled components is performed on a single integrated device capable of performing both the separation and detection steps. Various suitable instruments capable of performing such analyses are available including, for example, the Micro-Channel Plate available from Hewlett-Packard and MegaBACE from Molecular Dynamics, or ABI Prism Sequencers from PE Biosystems (see also, Woolley, A. T. and Mathies, R. A., *Proc. Natl. Acad. Sci. USA*, 91:11348–11352 (1994)).

2. Homogeneous Assays

Other methods, however, are homogenous assay methods in which extension products do not need to be separated from other extension reaction components (e.g., unextended primer and unincorporated nucleotide). In certain methods, this is accomplished by using donor fluorophores that have low fluorescence quantum yield and high extinction coefficient in combination with acceptor fluorophores that do not strongly fluoresce at the wavelength at which the donor is excited. As used herein, the term "low fluorescence quantum yield and high extinction coefficient" refers to fluorophores that can absorb a large number of photons while emitting only a relatively low level of fluorescence. For example, the quantum yield of certain fluorophores within this category is less than 0.6, in other instances, less than 0.3 and in still other instances, less than 0.2 or 0.1. Fluorophores with a high extinction coefficient generally have extinction coefficients that are greater than or equal to 100,000 $M^{-1}$ $cm^{-1}$. In some intances, the extinction coefficient is greater than 200,000 $M^{-1}$ $cm^{-1}$, and, in still other instances, greater than 300,000 $M^{-1}$ $cm^{-1}$. Specific examples of such fluorophores include cyanine dyes, including, but not limited to, CYA, Cy2, Cy3, Cy5.5, Cy7 and Cy7.5 (see, e.g., Hung, et al., 1996).

Various acceptor dyes that do not strongly fluoresce at the excitation wavelength of the foregoing donor dyes can be utilized. For example, the cyanine dyes can be paired with various rhodamine dyes, including, but not limited to, ROX (6-carboxy-X-rhodamine), TAMRA (N,N,N',N'-tetramethyl-6-carboxyrhodamine), R110 (5&6-carboxyrhodamine-110), and R6G (6-carboxyrhodamine-6G). All these dyes are available from Molecular Probes, Eugene, Oreg. Some methods utilize CYA as a donor fluorophore in combination with rhodamine dyes.

3. Double-Stranded v. Single-Stranded Extension Product

The double-stranded ET-labeled extension product formed as a consequence of primer extension can be detected directly in certain methods. This is possible because the label on the primer is positioned so that upon incorporation of the labeled non-extendible nucleotide the donor and acceptor fluorophores are immediately spaced so as to be in an energy transfer relationship. Thus, energy transfer can be detected while the extended primer remains hybridized to the target nucleic acid. Unlike certain other methods, it is unnecessary to denature the extended primer from the target nucleic acid prior to detection of energy transfer.

In some instances, double-stranded extension product is denatured so that the extended primer is separated from the target nucleic acid. The strands can be separated using appropriate denaturing conditions and methods known in the art including, but not limited to, heat, alkali, formamide, urea, glyoxal, and combinations thereof. In some instances, single-stranded gel separation achieves higher resolution, thus permitting clearer and more distinct signal detection.

V. Genotyping

A. Generally

A diploid organism contains two copies of each gene. Genotyping of a diploid organism involves the determination of whether the organism contains two copies of the reference allele (a homozygote for the reference allele), one copy each of a reference and variant allele (i.e., a heterozygote), or contains two copies of the variant allele (i.e., a homozygote for the variant allele). When conducting a genotyping analysis, the methods of the invention can be utilized to interrogate a single variant site. However, as described infra in the section on multiplexing, the methods can also be used to determine the genotype of an individual in many different DNA loci, either on the same gene, different genes or combinations thereof.

The ability to use the methods of the invention to make rapid genotyping determinations provides a powerful tool in genetic analysis and ascertaining the susceptibility of an individual to a disease. Individuals that are homozygotes for an allele associated with a particular disease are at higher risk of obtaining the disease than a heterozygote, or a homozygote for an allele not associated with the disease. The heterozygote, however, is a carrier of the allele associated with the disease. Such knowledge can be useful in prenatal and other types of medical and genetic counseling, for example.

B. Biallelic Analysis

Most typically, SNPs consist of two allelic forms, i.e., the variant site includes one of two different nucleotides. A determination of which nucleotide is present at the variant site of each copy of the target nucleic acid can be done in various formats.

In one format, a sample containing target nucleic acid is divided between two reaction vessels. Primer bearing one member of a donor/acceptor fluorophore pair is added to each reaction vessel. One of two different non-extendible nucleotides, each complementary to one of the bases potentially at the variant site, is also added to each reaction vessel. The non-extendible nucleotides added to the different reaction vessels bear a fluorophore which together with the primer fluorophore form a donor/acceptor pair. The fluorophores borne by the non-extendible nucleotides added to the different reaction vessels can be the same or different. Although, typically if the sample is divided into two reactions, the different non-extendible nucleotides bear the same label. As described above for the general method, if the non-extendible nucleotide within the reaction vessels is complementary to the nucleotide at the variant site of the target nucleic acid, an ET-labeled extension product is formed. If the nucleotide is not complementary, ET-labeled extension product is not formed (FIG. 4). Following the extension reaction, samples are separately analyzed using any of the various methods described supra (e.g., by separating other components from potential extension product by gel electrophoresis and then detecting the presence or absence of ET-labeled product).

In a second format, differentially labeled non-extendible nucleotides are added to a single reaction vessel containing the target nucleic acid. With this approach, the non-extendible nucleotides bear different and distinguishable donor or acceptor fluorophores that have different excitation or emission spectra. This permits the different alleles to be discriminated on the basis of the color of the ET-labeled extension product(s) formed.

C. Triallelic and Tetrallelic Analyses

For polymorphisms that include more than two allelic forms, additional labeled non-extendible nucleotides can be used. For example, for triallelic polymorphisms, three differentially labeled nucleotides can be used. In like manner, with tetraallelic polymorphisms, four differentially labeled non-extendible nucleotides can be employed. If the different non-extendible nucleotides are differentially labeled, then extension reactions can be carried out in a single reaction vessel. If, however, the non-extendible nucleotides are not differentially labeled, then the number of reactions into which the sample is divided is equivalent to the number of allelic forms to be interrogated. Thus, for a triallelic study, the sample is divided into three separate reactions; for a tetraallelic investigation, the sample is divided into four separate reactions.

D. Example: Production of ET-dye Labeled SNP Extension Products

Initially, nucleotide regions containing a polymorphism to be analyzed are amplified using standard PCR methods, such as described infra in the section on sample preparation. To form ET-labeled products, single base primer extension of the donor CYA-labeled primers is performed in the presence of acceptor-labeled ddNTP terminators (see FIG. 1A). An alternative way to produce ET-labeled products is by using acceptor-labeled primer incorporated with donor-labeled terminator (see FIG. 1B). In both cases, ET-labeled SNP products are formed with donor-acceptor fluorophore pairs separated by 6 intervening bases. The particular labeled terminator used depends upon the different alleles being tested. For example, in the case in which a particular SNP includes an A allele and a G allele, the base for the labeled terminator would be T and C, respectively.

VI. Multiplexing

A. Different Variant Sites

The basic methods described above can be extended in a straightforward manner to multiplexing formats in which one or more steps in identifying the nucleotide at multiple variant sites are combined. Such formats allow for high throughput analysis of many loci.

If the different variant sites to be interrogated are different sites on the same target nucleic acid or different sites on different target nucleic acids, all the necessary extension reactions can be conducted in a single reaction vessel, provided the extension products formed from different variant sites are differentially encoded. Essentially, such methods involve pooling several single nucleotide extension reactions into a single reaction. The multiple sites being interrogated can be multiple sites on the same target nucleic acid, such sites being within the same gene or at sites in different genes. Alternatively, the multiple sites can be multiple different sites on target nucleic acids from different individuals.

Such multiplexing methods closely parallel the general methods described supra. Different primers for each of the different variant sites are annealed to their respective binding sites. The general structure of the primers and the methods for conducting the extension reactions is as set forth above. Here too, the particular labeled non-extendible nucleotide incorporated into the extended primer serves to identify the nucleotide present at the variant site.

In order to correlate the multiple extension products with the various sites, a number of different strategies can be utilized to aid in determining which extension product corresponds with which variant site. One option is to differentially label the non-extendible nucleotides such that different labels are used for different variant sites. Alternatively, primers can be tagged with distinctive secondary labels. A number of different secondary labels can be utilized. Such secondary labels can be any type of molecule or compound that is detectable. Suitable secondary labels include, but are not limited to, mass labels, radioisotopes, fluorophores (selected to not interfere with excitation and emission of the donor and acceptor fluorophores), chromophores, electron dense agents and magnetic particles. If mass labels are utilized, essentially any molecule that can be attached to the primer to increase its molecular weight are suitable. Specific examples include, multiple sugars, linked nucleosides such as adenosine or essentially any other type of monomer that can be linked to form modules of varying molecular weight.

The methods utilizing primers bearing secondary labels can be used in conjunction with the scheme in which different fluorophores are used for different variant. In this way, extension products can be identified and distinguished from one another on the basis of two criteria rather than simply one criterion. For example, in some methods, different non-extendible nucleotides are attached to different fluorophores. Further, primers include different secondary labels for different variant sites. The different extension products can then be identified and/or separated both according to the different secondary labels and the characteristic emissions of the different fluorophores.

B. Same Variant Site for Different Subjects

Certain aspects of the methods can be combined even when the same variant site (e.g., the same SNP) is to be examined for samples from multiple subjects. In this instance, separate extension reactions are conducted for each subject. Separate reactions are required since the primers used are the same. If reactions were conducted in a single reaction vessel, one could not distinguish which extension product was generated from which individual. Nonetheless, if differentially labeled primers and/or non-extendible nucleotides are used to encode for different individuals (i.e., different extension reactions), the extension products from the different extension reactions can be pooled and analyzed simultaneously. In certain methods, this is accomplished by using different sized primers for each extension reaction. Thus, different sized extension products are formed for different individuals, thus enabling the extension products from different subjects to be size separated (e.g., by gel electrophoresis). By combining different sized primers with differentially labeled non-extendible nucleotides for each reaction, one can also discriminate between extension products from different subjects on the basis of the color of the extension product.

C. Application to Multiplex SNP Analysis

Multiplexing of SNP assays through size discrimination can be achieved by using "multiplexing modules" to adjust primer lengths. The modules can be multiple units of a sugar (SS and SSSS) (Ju et al., 1996b), adenosine (AA and AAAA), or other kinds of building blocks. One can also build up multiplexing modules from synthetic universal modules that bear multi-functional groups for stepwise conjugation. Molecules that contain quaternary amines, amino and carboxylic acid groups are good candidates. These kinds of modules can be used to adjust not only the primer size but also the overall charge of primer to optimize the separation of the products.

Figure 5A:
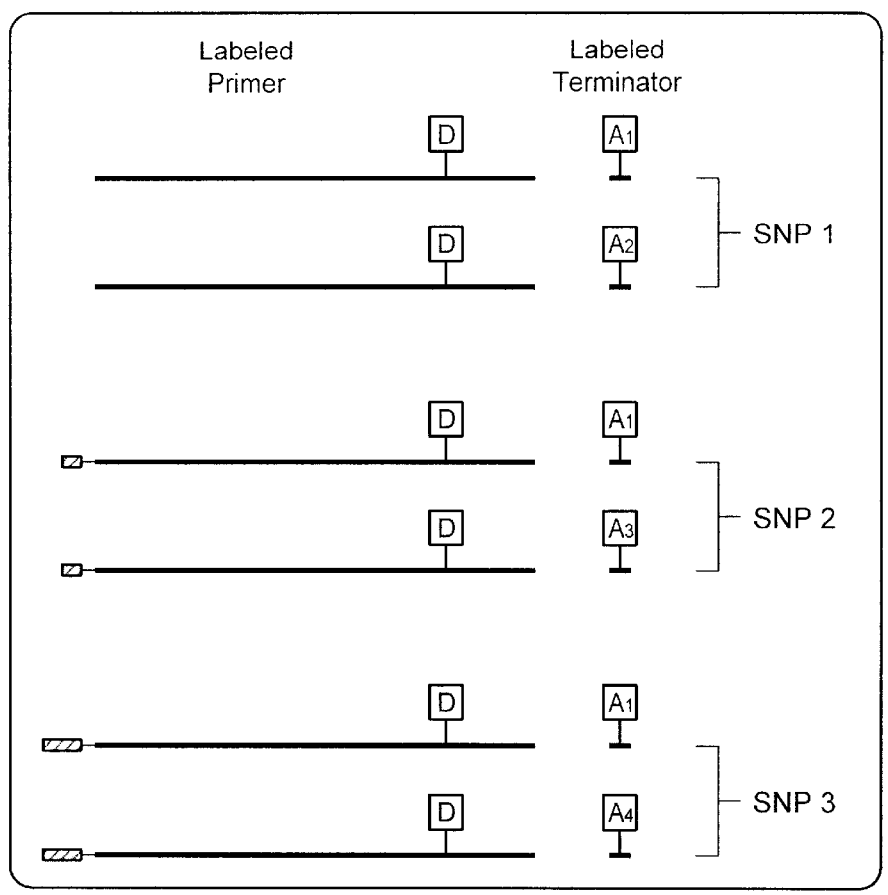
FIGS. 5A–5B illustrate a specific example of a multiplex SNP diagnostics with discrimination between different products by size and by multiple-color labeling. Multiplexing modules varying in size (represented by dashed box) are used to adjust primer sizes. Cyanine CYA is used as donor (D), while rhodamine dyes R110 ($A_1$), R6G ($A_2$), TAMRA ($A_3$) and ROX ($A_4$) are used as acceptors. In this assay, three SNP analyses can be performed in one lane.
Figure 5B:
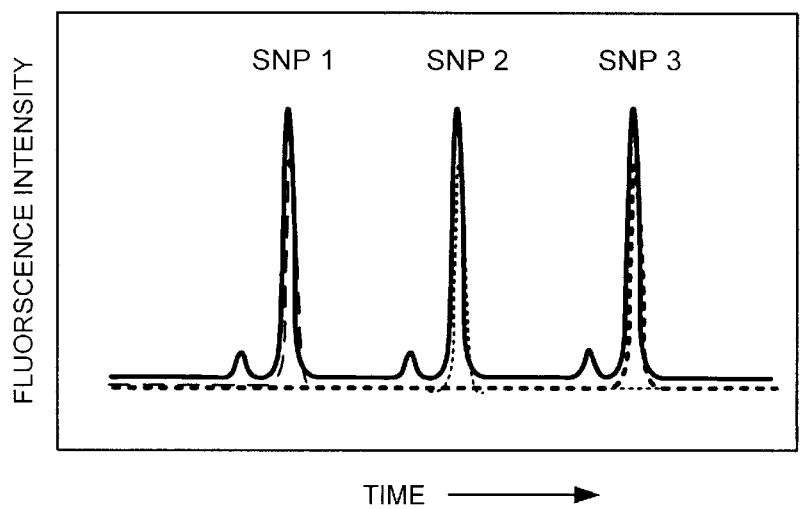
Figure 5C:
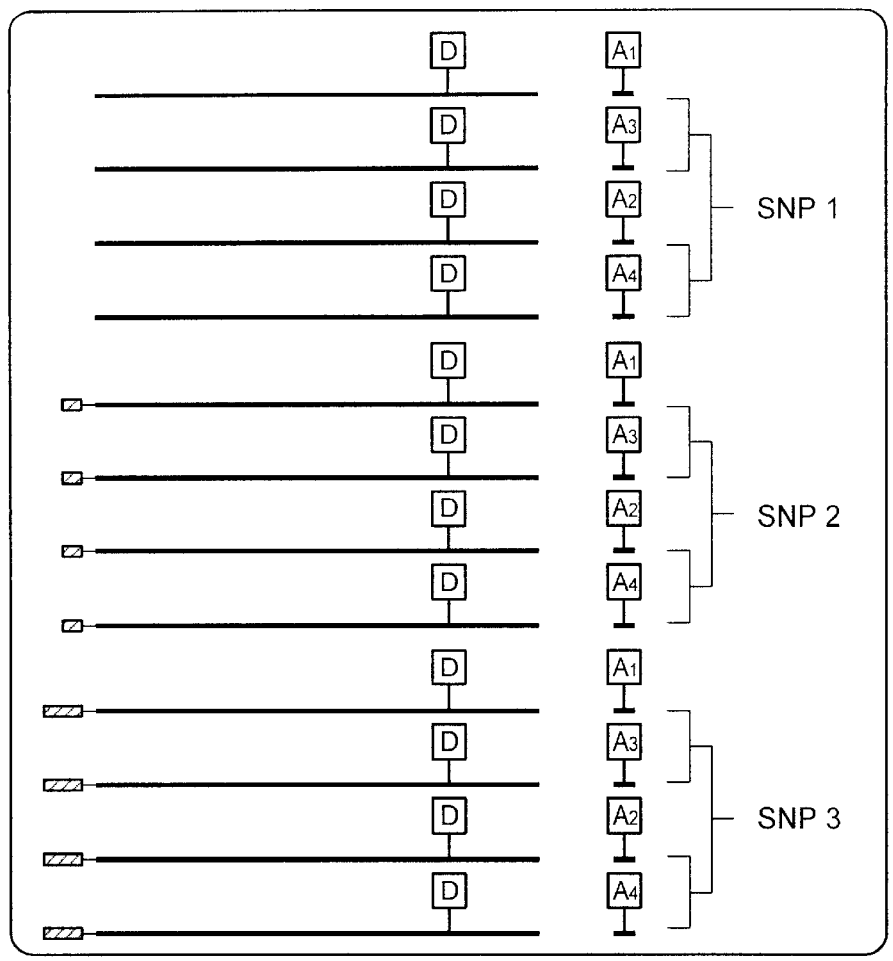
FIGS. 5C–5D illustrate a specific example of a multiplex SNP diagnostic with discrimination between different products by size and with multiple-color labeling. Multiplexing modules varying in size (represented by dashed box) are used to adjust primer sizes. Cyanine CYA is used as donor (D), while rhodamine dyes R110 ($A_1$), R6G ($A_2$), TAMRA ($A_3$) and ROX ($A_4$) are used as acceptors. In this assay, six SNP analyses can be performed in one lane.

The ability to discriminate between different extension fragments through the use of "multiplexing modules" separately or in combination with the multiple emission color combinations made possible by the distinctive FRET signal generated by using different acceptor dyes allows multiplex SNP analyses (see FIGS. 5A and 5C; different sized modules represented by dashed segments). Each SNP assay contains donor-labeled primers and two or more acceptor-labeled ddNTPs. SNP extension products can be separated according to the difference in primer sizes (see FIGS. 5B and 5D). The methods of the present invention can also be used to obtain different colors for different SNPs in a single electrophoretic separation lane. Single-tube SNP assay for multiplex extension can be accomplished by combining allele-specific PCR with the discrimination between amplification products by their sizes.

In the analysis depicted in FIG. 5A, two differentially labeled non-extendible nucleotides (terminators) are used; these are complementary to the nucleotides potentially at a biallelic site. Different SNPs can be distinguished both by differences in the molecular weight of extension products and color. The analysis in FIG. 5C is the same, except four differentially labeled non-extendible nucleotides are used to cover all possible nucleotides at a variant site.

The different primers shown in FIGS. 5A and 5C can be in the same gene or in different genes. Furthermore, using the different combinations of donor and acceptor dyes to create different emission colors, as well as the different size-adjusting modules, either separately or in combination, multiple SNP analyses can be conducted simultaneously, wherein the different SNP sites represent different loci from one subject or the same loci from different subjects.

Figure 5D:
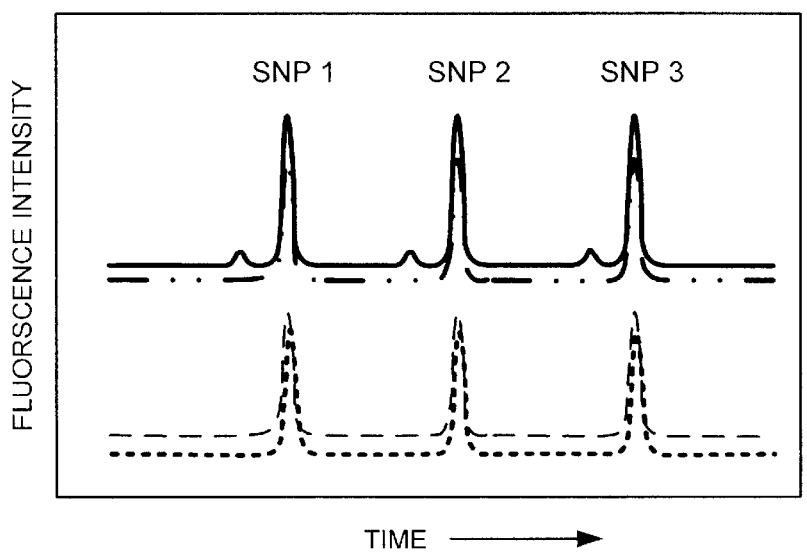

Although it is preferred to use both size differences and color differences to distinguish between different SNPs, the different SNPs within a single sample can be differentiated by size or color alone. Preferably, however, different SNPs are distinguished one from another on the basis of both size and color. For example, even though the different SNPs can be distinguished by size as illustrated in FIGS. 5B and 5D, the absence of an expected color can serve as an indicator that the assay for a particular SNP failed. More specifically, by designing an analysis so that each SNP is associated with a particular color pair, the absence of a particular color indicates which specific SNP test failed. This type of assessment has not been possible prior to the present invention.

The new labeling method provided for by the present invention for SNP genotyping provides enhanced signal intensities and excellent color discrimination between target and unincorporated reagents, especially compared to other related methods. Improvements in the quality of the data allow the amount of sample to be scaled down and the use of high throughput microplate electrophoresis separations. Scaling down of the amount of sample also decreases reagent consumption with reduction in assay cost. These improvements in data quality also allow the development of simpler and more robust SNP calling algorithms.

VII. Samples

A. Types of Target Nucleic Acids

The methods of the present invention can be utilized to determine the identity of a nucleotide at a variety of different types of variant sites including, but not limited to, SNPs and mutations such as transitions, transversions, insertions and deletions. The presence or absence of a target nucleic acid in a sample can be detected generally as the presence or absence of a particular nucleotide. Individual nucleotides located at a particular site can also be identified by the methods described herein.

The methods presented are generally applicable to deoxyribonucleic acids, ribonucleic acids, or copolymers thereof. The nucleic acids can be single-stranded or double-stranded. The target nucleic acid can include non-naturally occurring nucleotide analogs including, for example, deoxyinosine or 7-deasa-2-deoxyguanosine. Such analogs destabilize duplex DNA and allow a primer annealing and extension reaction to occur in double-stranded nucleic acids without completely separating the two strands. In some instances, RNA samples are first reversed transcribed to form cDNA before use.

The target nucleic acid can be only a fraction of a larger nucleic acid or can be present initially as a purified and discrete molecule. Additionally, the target nucleic acid can constitute the entire nucleic acid or can be a fraction of a complex mixture of nucleic acids. The target nucleic acid can be synthesized enzymatically in vivo, synthesized enzymatically in vitro, or synthesized non-enzymatically.

B. Sources

The target nucleic acid can be from any source. The samples that include the target nucleic acids can be natural or synthetic using enzymatic or synthetic organic techniques. Likewise, the sample can be taken from any organism, including but not limited to, plants, microorganisms (e.g., bacteria, fungi and viruses), vertebrates, invertebrates and mammals (e.g., humans, primates, horses, dogs, cows, pigs and sheep).

For assay of genomic DNA, virtually any biological sample (other than pure red blood cells) is suitable. Samples can be obtained from the tissues or fluids of an organism; samples can also be obtained from cell cultures, tissue homogenates or synthesized as described above. For example, samples can be obtained from whole blood, serum, semen, saliva, tears, urine, fecal material, sweat, buccal, skin, spinal fluid and hair. Samples can also be derived from in vitro cell cultures, including the growth medium, recombinant cells and cell components. For assay of cDNA or mRNA reverse transcribed to form cDNA, the tissue sample is obtained from an organ in which the target nucleic acid is expressed. For example, if the target nucleic acid is a cytochrome P450, the liver is a suitable source. Samples for use in prenatal testing can be obtained from amniotic fluid.

The target nucleic acid(s) can also be obtained from non-living sources suspected of containing matter from living organisms. For example, in the instance of samples obtained for forensic analysis, the target nucleic acids can be obtained from samples of clothing, furniture, weapons and other items found at a crime scene.

C. Sample Preparation/Amplification

In some instances, the samples contain such a low level of target nucleic acids that it is useful to conduct a pre-amplification reaction to increase the concentration of the target nucleic acids. If samples are to be amplified, amplification is typically conducted using the polymerase chain reaction (PCR) according to known procedures. See generally, *PCR Technology: Principles and Applications for DNA Amplification* (H. A. Erlich, Ed.) Freeman Press, NY, N.Y. (1992); *PCR Protocols: A Guide to Methods and*

Applications (Innis, et al., Eds.) Academic Press, San Diego, Calif. (1990); Mattila et al., *Nucleic Acids Res.* 19: 4967 (1991); Eckert et al., *PCR Methods and Applications* 1: 17 (1991); *PCR* (McPherson et al. Ed.), IRL Press, Oxford); and U.S. Pat. Nos. 4,683,202 and 4,683,195, each of which is incorporated by reference in its entirety. Other suitable amplification methods include the ligase chain reaction (LCR) (see Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), and self-sustained sequence replication (Guatelli et al., *Proc. Nat. Acad. Sci. USA,* 87:1874 (1990)) and nucleic acid based sequence amplification (NASBA; Sooknanan, R. and Malek, L., *Bio/Technology* 13: 563–65 (1995)), each of which are incorporated by reference in their entirety.

Further guidance regarding nucleic sample preparation is described in Sambrook, et al., *Molecular Cloning: A Laboratory Manual,* $2^{nd}$ Ed., Cold Spring Harbor Laboratory Press, (1989), which is incorporated herein by reference in its entirety.

VIII. Primers

A. Type

A variety of different types of primers can be utilized with the present methods. Suitable primers include, for example, an oligodeoxyribonucleotide, an oligoribonucleotide, a protein nucleic acid or a copolymer thereof. Primers can be either naturally occurring nucleic acids or prepared using synthetic methods. If synthesized, the primers can be synthesized either enzymatically in vitro, enzymatically in vivo or non-enzymatically in vitro.

Depending upon the nature of the target nucleic acid (see section on samples infra) various combinations of primer/target nucleic acid duplexes can be formed. For example, in some methods the template is a deoxyribonucleic acid and the primer is an oligodeoxyribonucleotide, an oligoribonucleotide, or a copolymer thereof. In such instances, a DNA polymerase is utilized to generate a DNA product. In certain other methods, the template is a ribonucleic acid and the primer is an oligodeoxyribonucleotide, an oligoribonucleotide, or a copolymer thereof. Reverse transcriptase can be utilized to form a DNA product. In yet other methods, the template is a deoxyribonucleic acid and the primer is an oligoribonucleotide. Added RNA polymerase can produce an RNA product from such a duplex. Finally, if the template is a ribonucleic acid and the primer an oligoribonucleotide, then an RNA replicase can form an RNA product.

B. Size/composition

Primers are sufficiently long to specifically bind or hybridize to the appropriate target nucleic acid and to form a stable hybridization complex under the extension reaction conditions. Typically, the primers are 15 to 30 nucleotides in length; in other instances, the primers are 20 to 24 nucleotides long. The length of the primers can be adjusted to be longer or somewhat shorter depending upon the particular sequence to which a primer hybridizes (e.g., primers with a high G/C content typically can be shorter than those with a low G/C content).

The term "specifically hybridize" or "specifically bind" when used in reference to a primer and a complementary target nucleic acid means that formation of a hybrid between the primer and a particular target nucleic acid in which the primer preferentially hybridizes to the target nucleic acid over nucleic acids other than the target nucleic acid. Most typically, the primers are designed to be perfectly complementary over their entire length with the template strand. However, in certain methods the primers are substantially complementary to the target nucleic acid; mismatches in such instances, however, should not adversely affect the stability of the primer/target nucleic acid hybridization complex.

The stringency of hybridization is determined by a number of factors including temperature, ionic strength, length of time and concentration of certain agents such as formamide. These factors and others are discussed in, for example, Sambrook, et al., *Molecular Cloning: A Laboratory Manual,* $2^{nd}$ Ed., Cold Spring Harbor Laboratory Press, (1989).

In certain methods, the primer can include a moiety that allows for the affinity separation of the extension product or primer from unincorporated reagents and/or the target nucleic acid and/or other nucleic acids in the test sample. For example, the primer can include biotin which permits the affinity separation of the primer or extension product from other reaction components through binding of biotin to avidin or streptavidin molecules attached to a solid support. As another example, a support can be attached to a nucleic acid sequence that is complementary to the primer or extension product generated therefrom. Hybridization between the primer and its complementary sequence also allows for affinity separation.

C. Synthesis and Labeling

1. Materials

Active N-hydroxysuccinimide (NHS) ester of 3-($\epsilon$-carboxypentyl)-3'-ethyl-5,5'-dimethyloxacarbocyanine (CYA) can be synthesized as previously described (Hung et al., 1996). Chemicals used for the synthesis of oligonucleotides can be purchased from Applied Biosystems Division of Perkin Elmer Corporation (Foster City, Calif.). 5'-dimethoxytrityl-5-[N-(trifluoroacetylaminohexyl)-3-acrylimido]-2'-deoxyuridine,3'-[(2-cyanoethyl)-(N,N-diisopropyl)]-phosphoramidite (Amino-Modifier C6 dT) can be obtained from Glen Research (Sterling, Va.). Uni-Link AminoModifier can be obtained from Clontech (Palo Alto, Calif.). Oligodeoxynucleotides can be synthesized by the phosphoramidite method on a nucleic acid synthesizer. Single dye labeled R110-ddNTPs, R6G-ddNTPs, TAMRA-ddNTPs and ROX-ddNTPs can be purchased from DuPont NEN (Boston, Mass.).

2. Primer Labeling

Certain labeled primers can be purchased from a variety of commercial sources. Alternatively, labels can be attached to a primer nucleotide in a number of different ways. One general approach involves preparing derivatives of dyes that contain appropriate functional groups for linking the dyes to the detection primer. Such methods are described, for example, by Marshall, *Histochemical J.* 7:299–303 (1975); Mechnen et al. in U.S. Pat. No. 5,188,934; Bergot et al. in PCT publication PCT/US90/05565; Ullman et al. in U.S. Pat. No. 3,996,345 and Khanna et al. in U.S. Pat. No. 4,351,760. Primers can be labeled internally or by end labeling according to established methods (see, e.g., Ju et al., *Proc. Natl. Acad. Sci.* 92:4347–4351 (1995); Nelson et al., *Nuc. Acids Res.* 20:6253–6259 (1992), which are incorporated by reference in their entirety).

In other instances, the fluorophore is borne by a nucleotide substitute or a modified nucleotide. As used herein, a nucleotide substitute and modified nucleotides are defined as a molecule that is: 1) a non-naturally occurring nucleotide, 2) can be incorporated into primer sequence without interfering with the ability of the primer to selectively hybridize with its binding site, and 3) provides a functional group to which a fluorophore can be attached. Typically, the functional group is attached to a chain/linker, such as a hydrocarbon chain of several carbons in length. Modified nucleotides typically include a ribose sugar linked to a purine or pyrimidine base. A nucleotide substitute typically lacks the ribose and/or nucleotide base. Specific examples of a modified nucleotide include modified thymidine T* (see FIG. 2B); specific examples of nucleotide substitutes include a variety of commercial available universal linkers such as Uni-Link AminoModifier (see FIG. 2C).

More specifically, in some instances, a label is linked to a nucleotide in the detection primer via a linker. A number of such linkers are commercially available and have varying lengths. Such linkers are useful for obtaining a desired distance between the primer and label to ensure that the label does not interfere with the extension reactions. In general such linkers include a functional group (e.g., amino, hydroxyl, sulfhydryl, carboxyl) at each end so that one end can be attached to a nucleotide in the detection primer and the other end attached to the label (e.g., fluorescent molecule). Examples of such linkers for end-labeling include "Amino Modifier C3", "Amino Modifier C6," "Amino Modified C7" and "Amino Modified C12" that are available from Operon Technologies, Inc. Moreover, a suitable linker for the internal-labeling is the "Uni-Link Amino Modifier" available from Clonetech (Palo Alto, Calif.).

Alternatively, modified nucleotides designed to allow for attachment of a label can be incorporated into the detection primer during synthesis. Examples of such modified nucleotides include, for example, "Amino-Modifier C6 dT" and similar modified nucleotides available from Glen Research (Sterling, Va.) and designed to function as modified thymidine nucleotides (see, e.g., "Users Guide to DNA Modification," Glen Research Corporation, pp. 1–68 (1996), which is incorporated by reference in its entirety). Similarly modified deoxycytidine compounds can also be utilized (see, e.g., Markiewicz, W. T., et al., *Nucleosides and Nucleotides*, 11:1703–1711 (1992), which is incorporated by reference in its entirety). These molecules typically contain a protected primary amine that can serve as the attachment site of a label (e.g., a fluorescent label) following deprotection. Methods for incorporating such modified nucleotides into a primer are described, for example, in U.S. Pat. Nos. 5,654,419; 5,688,648; 5,853,992; and 5,728,528 to Mathies et al. and Glazer et al. Single dye labeled R110-ddNTPs, R6G-ddNTPs, TAMRA-ddNTPs and ROX-ddNTPs can be purchased from DuPont NEN (Boston, Mass.).

In other instances in which label is attached during synthesis, prelabeled nucleotides (e.g., TAMRA-dT or Dabcyl-dT can be obtained commercially (e.g., Glen Research, Sterling, Va.)) are obtained in functionalized form (e.g., as a phosphoramidite) and are incorporated during organic synthesis. Radioactive label can be incorporated in a similar manner.

Figure 2A:
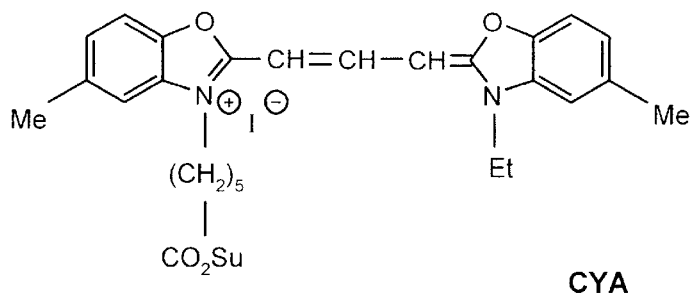
FIGS. 2A–2C show the structures of the certain components of the donor dye-labeled primer for certain assays of the invention. D: donor cyanine dye, CYA (FIG. 2A); T*: modified thymidine, AminoModifier C6dT (FIG. 2B); and N: substituted amino linker, Uni-Link AminoModifier (FIG. 2C).
Figure 2B:
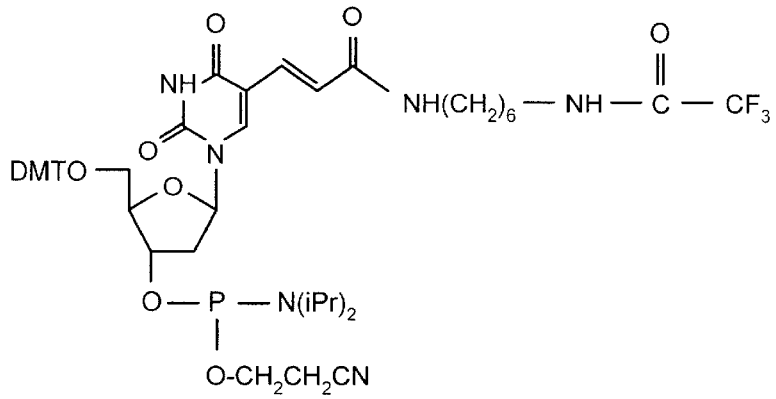
Figure 2C:
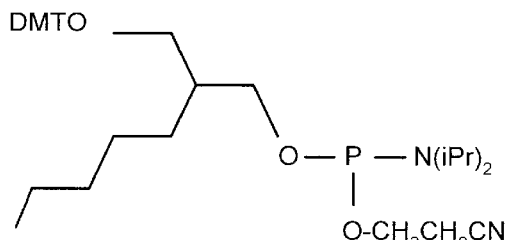

For the design of dye-labeled primers for assaying variant sites, a thymidine base (T) at the third to tenth positions from the 3'-end of the candidate primer sequence provides good results. This thymidine base is replaced by a modified thymidine (T*) which has an amino linker arm to attach the dye of choice. For those primers which have no T base positioned in the desired region, an Uni-Link AminoModifier (N) can be used in place of any base without changing the natural internucleotide phosphate distance. This Uni-Link AminoModifier (N) is a cyanoethyl phosphoramidite that provides an amino linker arm for dye labeling. Structures of the cyanine donor (CYA), modified thymidine (T*), and Uni-Link AminoModifier (N) are shown in FIGS. 2A–2C.

As a more specific example, ET primers with CYA as donor and a donor-acceptor spacing of 4–6 nucleotides, offer excellent acceptor emission intensities coupled with negligible donor emissions. In multiplex separation, this allows precise quantitation of the ratio of the signals from DNA fragments labeled with one or another of two different primers (Wang et al., 1997).

Crude primers from automated DNA synthesis can be purified by high performance liquid chromatography (HPLC) on, for example, a Bio-Rad Hi-Pore reversed-phase column using 0.1 M TEAA and $CH_3CN$ (Hung et al., 1998). Primers can then be conjugated with either donor dye (e.g., CYA) or acceptor dyes (e.g., R110, R6G, TAMRA and ROX).

Figure 3A:
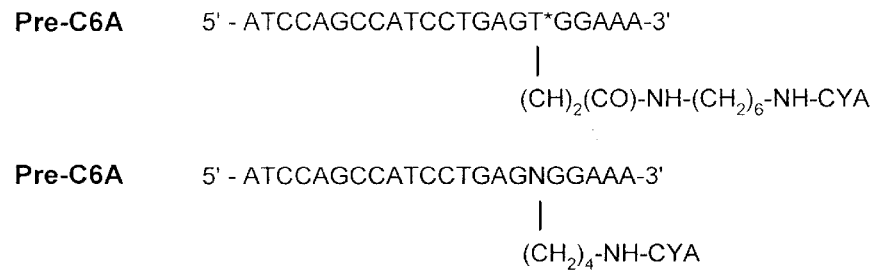
FIGS. 3A–3C illustrate the design and synthesis of cyanine (CYA) dye-labeled primers.
Figure 3B:
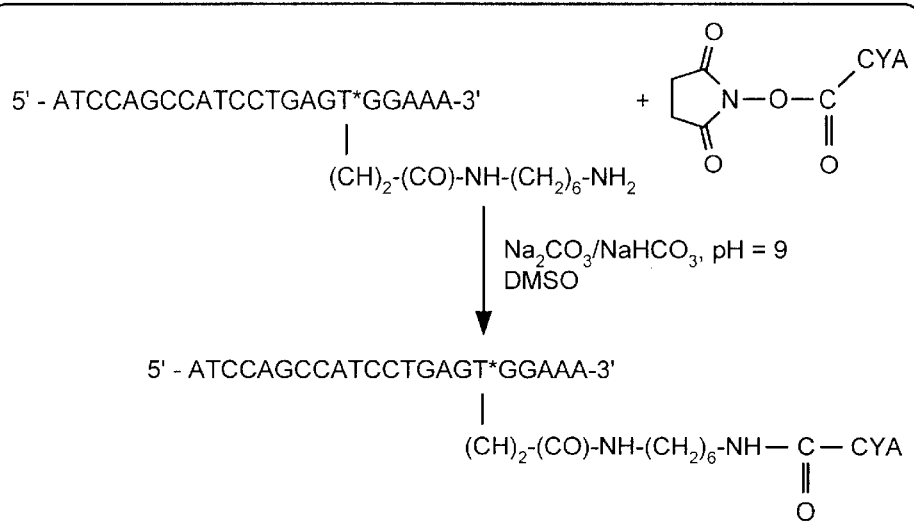
Figure 3C:
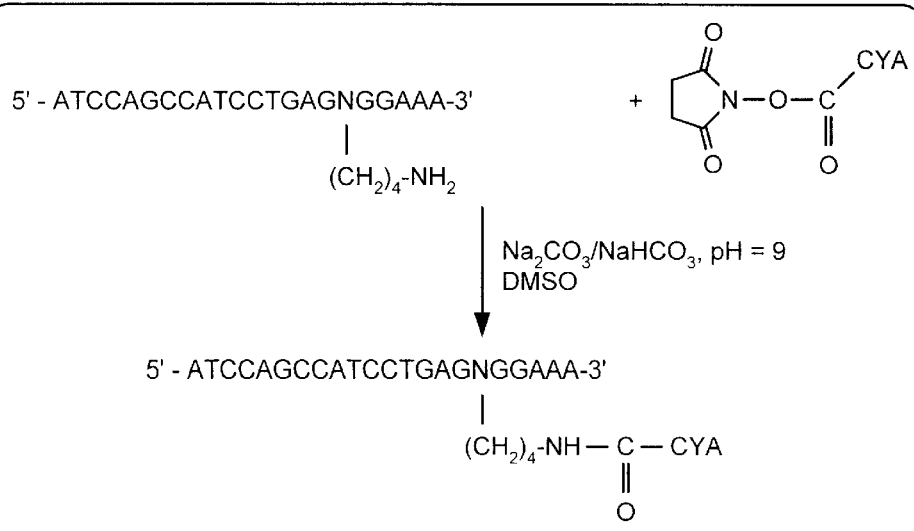

Two examples of the synthesis of CYA-labeled primers are presented in FIG. 3A and 3B. In these two cases, the original T base at the sixth position from the 3'-end is replaced by either T* or N. Dye conjugations are run in $NaHCO_3/Na_2CO_3$ buffer (pH 9.0) in presence of DMSO. The resulting CYA-labeled primers are precursors (the donor components), so-called Pre-C6A, of the energy transfer dye pairs resulting upon extension by addition of an acceptor dye-labeled ddNTP (see supra).

IX. Labeling

Various fluorescent dyes can serve as the donor and acceptor dyes that are used to label the primer and non-extendible nucleotide. One group of donor and acceptor dyes includes the xanthene dyes, such as fluorescein dyes, and rhodamine dyes. A variety of derivatives of these dyes are commercially available. Often functional groups are introduced into the phenyl group of these dyes to serve as a linkage site to an oligonucleotide. Another general group of dyes includes the naphthylamines which have an amino group in the alpha or beta position. Dyes of this general type include 1-dimethylaminonaphthyl-5-sulfonate, 1-anilino-8-naphthalende sulfonate and 2-p-touidinyl-6-naphthalene sulfonate. Other dyes include 3-phenyl-7-isocyanatocoumarin, acridines, such as 9-isothiocyanatoacridine and acridine orange, pyrenes, bensoxadiazoles and stilbenes. Additional dyes include 3-(ϵ-carboxypentyl)-3'-ethyl-5,5'-dimethyloxacarbocyanine (CYA), 6-carboxy fluorescein (FAM), 5&6-carboxyrhodamine-110 (R110), 6-carboxyrhodamine-6G (R6G), N,N,N',N'-tetramethyl-6-carboxyrhodamine (TAMRA), 6-carboxy-X-rhodamine (ROX), 6-carboxy-4', 5'-dichloro-2',7'-dimethoxyfluorescein (JOE), ALEXA Fluor™, Cy2, Texas Red and Rhodamine Red. Also, more fluorescent dyes are available from Applied Biosystems Division of Perkin Elmer Corporation (Foster City, Calif.), 6-carboxy-2',4,7,7'-tetrachlorofluorescein (TET), 6-carboxy-2',4,4',5',7,7'-hexachlorofluorescein (HEX), 5-carboxy-2',4',5',7'-tetrachlorofluorescein (ZOE), NAN, NED, and from Amersham Pharmacia Biotech (Piscataway, N.J.), Cy3, Cy3.5, Cy5, Cy5.5, Cy7, and Cy7.5.

As noted above, the fluorescent dyes are selected so that the emission spectrum of the donor fluorophore overlaps the excitation spectrum of the acceptor fluorophore. Furthermore, in some methods, a donor fluorophore having a high extinction coefficient and low fluorescence quantum yield is paired with an acceptor fluorophore that do not strongly emit at the excitation wavelength of the donor fluorophore. A cyanine donor (e.g., CYA) and a rhodamine dye (e.g., R110, R6G, TAMRA and ROX) are an example of such a pair.

Further guidance regarding the selection of donor and acceptor pairs that can effectively be used with the methods of the present invention include: *Fluorescence Spectroscopy* (Pesce et al., Eds.) Marcel Dekker, New York, (1971); White et al., *Fluorescence Analysis: A Practical Approach*, Marcel Dekker, New York, (1970); Berlman, *Handbook of Fluorescence Spectra of Aromatic Molecules*, 2$^{nd}$ ed., Academic Press, New York, (1971); Griffiths, *Colour and Constitution of Organic Molecules*, Academic Press, New York, (1976); *Indicators* (Bishop, Ed.). Pergamon Press, Oxford, 19723; and Haugland, *Handbook of Fluorescent Probes and Research Chemicals*, Molecular Probes, Eugene (1992).

If the primer also bears a secondary label for use in multiplexing, the label can be selected from a number of different label types including, but not limited to, fluorophores, chromophores, molecules that chemiluminesce, magnetic particles, radioisotopes, mass markers, electron dense particles, enzymes, cofactors, electrochemically active molecules, substrates for enzymes and ligands having specific binding partners (e.g., avid/biotin).

X. Kits

The invention also provides kits for interrogating and/or detecting variant sites in target nucleic acids of interest. Such kits can be used in research, clinical and test laboratories to perform the methods of the invention. The kit typically includes one or more primers. Each primer is complementary to a different segment of a target nucleic acid of interest and hybridizes so that the 3'-end of the primer is adjacent to the variant site. Different primers in the kit selectively hybridize adjacent different variant sites. Each primer in the kit also bears a fluorophore that comprises one member of a donor/acceptor pair. Typically, the primers are selected for use in detecting one or more of the SNPs described in the following section. Generally, the kits include at least 2, 3, 4, or 5 primers. Other kits include more primers, such as at least 10, 15, 20 or 25 primers. The primers in the kits can be labeled at various positions, including either end or at an internal location and labeled at a modified nucleotide or nucleotide substitute as described supra. In certain instances, the primers include specific labels that have low fluorescence quantum yield, particularly the cyanine dyes and CYA as described above. The primers in the kit optionally include a secondary label for use in multiplexing reactions.

The kits typically contain one or more non-extendible nucleotides that bear a fluorophore that comprises the other member of the donor/acceptor pair to go with the member attached to the primer. The non-extendible nucleotides are selected to be complementary with the nucleotides potentially at the variant site of the target nucleic acids of interest.

The kits can include various other components for conducting template-dependent extension reactions including, for example, a polymerase and buffers. Kits can also include the necessary electrophoretic components to size separate the extension products formed during an analysis. Such components include gel polymers, polymerizing agents and buffers. Typically, the kits include containers for housing the various components and instructions for using the components of the kit to conduct an analysis.

XI. Exemplary Utilities

The methods, compositions and kits of the invention are generally useful for determining the identity of a nucleotide at a variant site. These methods, however, find use in a variety of more specific applications. One use is the identification and detection of point mutations (e.g., somatic point mutations), specifically those mutations correlated with diseases. For example, the methods described herein are useful for identifying whether a nucleic acid from a particular subject includes a reference allele or a variant allele at a particular SNP site. Furthermore, the methods can be utilized to establish the genotype of the individual being tested (i.e., distinguish whether the individual is a homozygote for the reference allele, a heterozygote or a homozygote for the variant allele).

The genotyping utility of the present methods makes them useful within the context of medical diagnosis and prognosis. Since many SNPs are associated with various diseases, clinicians can utilize the results of the genotype study to assess the presence of disease, whether an individual is a carrier of disease, the likelihood that an individual will get a particular disease and the likely efficacy of various treatment alternatives.

The methods also have a variety of non-medical uses. Such utilities include detecting pathogenic microorganisms, paternity testing and forensic analysis. The methods can also be used to identify SNPs in non-humans, including for example plants, bacteria and viruses.

These various uses are described more fully below.

A. Correlation Studies

Use of the methods of the present invention to acquire diagnostic information involves obtaining a sample from a number of different individuals known to have a common disease and conducting screening tests to determine whether they consistently share a common genotype at one or more SNP sites. The results of such screening can be used to establish correlations between certain genotypes and certain diseases.

In a related fashion, the methods of the invention can be used to develop correlations between certain genotypes and patient prognosis. For example, the genotype of a population of individuals suffering from a common disease can be determined at one or more SNP sites. The health history of the individuals can be monitored with time to establish correlations between certain genotypes and disease outcomes.

The methods of the invention can also be used to formulate optimal treatment protocols for a particular disease. The methods described herein can be used to place individuals into groups that share a common phenotype and genotype. The group can then be subdivided into various groups that each receive different forms of treatment. By monitoring the health status of the different treatment groups over time, the most effective treatment program for a particular genotype can be established.

B. Use of Current Methods as Screening and Therapeutic Tool

In instances in which a correlation between a particular genotype and disease state have already been established, the methods of the invention can be utilized as a diagnostic tool, a prognostic tool and as a means for assessing the success of various treatment options.

For patients having symptoms of a disease, the methods of the present invention can be used to determine if the patient has a genotype known to be associated with a disease that commonly causes the symptoms the patient exhibits.

For example, if the genotyping methods of the invention show that the individual has a genotype associated with a particular disease and further that the genotype is associated with poor recovery (e.g., a mutant homozygote), the physician can counsel the client regarding the likely effectiveness of aggressive treatment options and the option of simply foregoing such treatments, especially if the disease is quite advanced. On the other hand, if the genotype is associated with good recovery, the physician can describe a range of treatment options varying from simply monitoring the disease to see if the condition worsens or more aggressive measures to ensure that the disease is attacked before it gets worse.

The methods of the present invention are also valuable for assessing the actual risk of an individual known to be susceptible to acquiring a disease (e.g., an individual coming from a family that has a history of suffering from a disease). By determining whether the individual is a homozygote for the SNP associated with the disease or a heterozygote, a physician can more accurately assess and counsel the patient regarding the likelihood that the patient will begin suffering from disease, factors involved in triggering the disease and the pros and cons regarding different treatment alternatives.

Similarly, certain methods of the invention can also be used to identify individuals at risk for disease, even though they have no symptoms of disease or no known susceptibilities to disease. An individual in this category would generally have no disease symptoms and have no family history of disease. In such cases, the methods of the present invention can be utilized as a useful preventive screening tool. Using the methods of the present invention, a number of selected SNP sites known to be associated with certain diseases can be interrogated to identify the genotype of the individual at those sites. If a particular genotype were identified that was known to be associated with a particular disease, then a physician could advise the individual regarding the likelihood that the disease would manifest itself and the range of treatment options available.

C. Examples of Diseases that can be Monitored

A large number of diseases have been shown to be correlated with particular allelic forms of SNPs. A large number of such SNPs are listed in WO 93/02216 and by Cooper et al. (*Hum. Genet.* 85:55–74 (1990)), both of which are incorporated herein by reference in their entirety. Specific examples of diseases associated with SNPs include: sickle cell anemia and B-thalassemias (mutation in β-globin gene; Antonarakis, *New Eng. J. Med.,* 320:153–163 (1989)), cystic fibrosis (mutation in cystic fibrosis transmembrane receptor (CFTR); see Kerem, et al., *Science* 245:1073–1080 (1989)), hyperlipoproteinemia (mutation in apolipoprotein E gene; see Mahley, *Science* 240:622–630 (1988)), a wide variety of autoimmune diseases (mutations in human major histocompatibility complex; see Thomson, *Ann. Rev. Genet.,* 22:31–50 (1988); Morel et al., *Proc. Nat. Acad. Sci. USA,* 85:8111–8115 (1988); and Scharf, et al., *Proc. Nat. Acad. Sci. USA,* 85:3504–3508 (1988)) and the formation of oncogenes (mutations to the human ras-gene family; see, e.g., Bos et al., *Nature,* 315:726–730 (1985); Farr et al., *Proc. Natl. Acad. Sci. USA,* 85:1629–1633 (1988); and Neri, et al., *Proc. Natl. Acad. Sci. USA,* 85:9268–9272 (1988)). Other genes containing SNPs associated with disease include genes encoding for angiotensinogen, angiotensin converting enzyme, cholesterol ester transfer protein, dopamine receptors, serotonin receptors, and HIV reverse transcriptase (RT).

D. Other Uses

The methods described herein can also be used to identify point mutations in microorganisms that could potentially result in altered pathogenicity or resistance to certain therapeutics. The methods can also be used to identify cells and strains having a desired genetic constitution for use in various biotechnology applications. The methods described herein can also detect the presence of somatic mutations that can result in various diseases, including cancer for example.

With knowledge gained from the genotyping methods described herein, clinicians can conduct prenatal testing using cells obtained from a fetus to check for a variety of inheritable diseases, such as those diseases associated with the SNPs listed above. The methods can also be used to identify carriers of mutant alleles. Such information can be of use by a couple prior to conception as they evaluate the risks of having a child with certain birth defects or inheritable diseases.

Methods of the invention can also be utilized in various identification applications, such as in the field of forensic medicine or paternal testing. In the case of forensic analysis, polymorphisms in specific genes can be determined in, for example, blood or semen obtained from a crime scene to indicate whether a particular suspect was involved in the crime. In like manner, polymorphism analysis may be utilized in paternity disputes to aid in determining whether a particular individual is the father of a certain child.

In another application, certain methods of the invention are used in blood typing or tissue classification. Tissue classifications, for example, can be determined by identifying polymorphisms specific for a particular individual.

BIBLIOGRAPHY

Brand, E., Chatelain, N., Mulatero, P., Féry, I., Curnow, K., Jeunemaitre, X., Corvol, P., Pascoe, L., and Soubrier, F. (1998) Structural analysis and evaluation of the aldosterone synthase gene in hypertension. *Hypertension* 32: 198–204.

Chen, X and Kwok, P. Y. (1997a) Template-directed dye-terminator incorporation (TDI) assay: a homogeneous DNA diagnostic method based on fluorescence resonance energy transfer. *Nucleic Acids Research* 25: 347–353.

Chen, X., Zehnbauer, B., Gnirke, A., and Kwok, P. Y. (1997b) Fluorescence energy transfer detection as a homogeneous DNA diagnostic method. *Proc. Natl. Acad. Sci. USA* 94:10756–10761.

Chen, X., Livak, K. J., and Kwok, P. Y. (1998) A homogeneous, ligase-mediated DNA diagnostic test. *Genome Research* 8: 549–556.

Chen, X. and Kwok, P. Y. (1999) Homogeneous genotyping assays for single nucleotide polymorphisms with fluorescence resonance energy transfer detection. *Genet. Anal.* 14:157–163.

Glazer, A. N., Mathies, R. A. (1997) Energy-transfer fluorescent reagents for DNA analyses. *Curr. Opin. Biotech.* 8: (1) 94–102.

Hung, S.-C., Ju, J., Mathies, R. A. and Glazer, A. N. (1996). Cyanine dyes with high absorption cross section as donor chromophores in energy transfer primers. *Anal. Biochem.* 243: 15–27.

Hung, S.-C., Mathies, R. A. and Glazer, A. N. (1997). Optimization of spectroscopic and electrophoretic properties of energy transfer primers. *Anal. Biochem.* 252: 78–88.

Hung, S.-C., Mathies, R. A. and Glazer, A. N. (1998). Comparison of fluorescent energy transfer primers with different donor-acceptor dye combinations. *Anal. Biochem.* 255: 32–38.

Ju, J., Kheterpal, I., Scherer, J. R., Ruan, C., Fuller, C. W., Glazer, A. N. and Mathies, R. A. (1995) Design and synthesis of fluorescence energy transfer dye-labeled primers and their application for DNA sequencing and analysis. *Anal. Biochem.* 231: 131–140.

Ju, J., Glazer, A. N. and Mathies, R. A. (1996a). Energy transfer primers: A new fluorescence labeling paradigm for DNA sequencing and analysis. *Nature Med.* 2: 246–249.

Ju, J., Glazer, A. N. and Mathies, R. A. (1996b). Cassette labeling for facile construction of energy transfer fluorescent primers. *Nucleic Acids Res.* 24: 1144–1148.

Risch, N. and Merikangas, K. (1996). The future of genetic studies of complex human diseases. *Science* 273: 1516–1517.

Wang, Y., Hung, S.-C., Linn, J. F., Steiner, G., Glazer, A. N., Sidransky, D. and Mathies, R. A. (1997). Microsatellite-based cancer detection using capillary array electrophoresis and energy-transfer fluorescent primers. *Electrophoresis* 18: 1742–1749.

Yu, H., Bowden, D. W., Spray, B. J., Rich, S. S., and Freedman, B. I. (1998) Identification of human plasma kallikrein gene polymorphisms and evaluation of their role in end-stage renal disease. *Hypertension* 31: 906–911.

U.S. Pat. No. 5,654,419. Design and Synthesis of Energy Transfer Fluorescent Dye Tagged Oligonucleotide Labels. Ju, J., Glazer, A. N., and Mathies, R. A., issued Aug. 5, 1997.

U.S. Pat. No. 5,688,648. Probes Labeled with Energy Transfer Coupled Dyes, Mathies, R. A., Glazer, A. N., and Ju, J., issued Nov. 18, 1997.

U.S. Pat. No. 5,707,804. Primers Labeled with Energy Transfer Coupled Dyes for DNA Sequencing, Mathies, R. A., Glazer, A. N., and Ju, J., issued Jan. 13, 1998.

U.S. Pat. No. 5,728,528. Universal Spacer/Energy Transfer Dyes. Mathies, R. A., Glazer, A. N., and Ju, J., issued Mar. 17, 1998.

U.S. Pat. No. 5,853,992. Cyanine Dyes with High Absorbance Cross-section as Donor Chromophores in Energy Transfer Primers. Glazer, A. N., Mathies, R. A., Hung, S.-C., and Ju, J., issued Dec. 29, 1998.

U.S. Pat. No. 5,945,283. Methods and Kits for Nucleic Acid Analysis Using Fluorescence Resonance Energy Transfer. Kwok, P.-Y. and Chen, X., issued Aug. 31, 1999.

WO 9722719. Method for Nucleic Acid Analysis Using Fluorescence Resonance Energy Transfer. Kwok, P.-Y. and Chen, X., 1996, published Jun. 26, 1997.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A method for analyzing a variant site of a target nucleic acid, comprising:

(a) hybridizing a primer bearing a first fluorophore to a segment of the target nucleic acid to form a labeled hybrid, wherein the 3'-end of the primer hybridizes to the target nucleic acid immediately adjacent to the variant site;

(b) conducting template-dependent extension of the primer in the presence of a polymerase and at least one non-extendible nucleotide bearing a second fluorophore, whereby a double-labeled extension product is formed if the non-extendible nucleotide is complementary to the nucleotide at the variant site and the first and second fluorophore borne by the extension product are brought into an energy transfer relationship while the extension product is hybridized to the target nucleic acid, wherein the first and second fluorophore comprise a donor and an acceptor fluorophore which have a donor-acceptor spacing in the extension product of less than 18 nucleotides; and (c) detecting the presence or absence of the double-labeled extension product, the presence or absence of double-labeled extension product indicating the identity of the nucleotide at the variant site.

2. The method of claim 1, wherein detecting comprises detecting double-labeled extension product while the primer remains hybridized to the target nucleic acid.

3. The method of claim 1, wherein detecting comprises optically exciting the donor fluorophore and detecting an increase in fluorescence emission by the acceptor fluorophore due to resonance energy transfer between the donor and acceptor fluorophore.

4. The method of claim 1, wherein detecting comprises optically exciting the donor fluorophore and detecting a decrease in fluorescence emission by the donor fluorophore due to resonance energy transfer between the donor and acceptor fluorophore.

5. The method of claim 1, further comprising separating the double-labeled extension product from other components in the extension reaction prior to detecting double-labeled extension product.

6. The method of claim 5, wherein separating comprises performing a size based separation.

7. The method of claim 6, wherein the size based separation is selected from the group of high performance liquid chromatograph (HPLC) and electrophoresis.

8. The method of claim 5, wherein the primer bears an attachment moiety and separating comprises allowing the primer to attach to a support via the attachment moiety.

9. The method of claim 1, wherein the donor fluorophore is selected from the group consisting of a cyanine dye and wherein the acceptor fluorophore is selected from the group consisting of R110, R6, TAMRA, ROX, FAM, JOE, ZOE, TET, HEX, NAN, Texas Red, and Rhodamine Red.

10. The method of claim 9, wherein the donor fluorophore is CYA.

11. The method of claim 1, wherein the donor fluorophore is attached to the primer and the acceptor fluorophore is attached to the non-extendible nucleotide.

12. The method of claim 1, wherein the acceptor fluorophore is attached to the primer and the donor fluorophore is attached to the non-extendible nucleotide.

13. The method of claim 1, wherein the first fluorophore is attached to an internal nucleotide, modified nucleotide or a nucleotide substitute.

14. The method of claim 13, wherein the nucleotide substitute or modified nucleotide is selected from the group consisting of a universal linker or modified thymidine.

15. The method of claim 1, wherein the donor-acceptor spacing is 3 to 10 nucleotides.

16. The method of claim 15, wherein the donor-acceptor spacing is 4 to 6 nucleotides.

17. The method of claim 1, wherein the non-extendible nucleotide is selected from the group consisting of an arabinoside triphosphate and a dideoxynucleotide.

18. The method of claim 17, wherein the non-extendible nucleotide is a dideoxynucleotide.

19. A method for determining the identity of a nucleotide at a variant site of a target nucleic acid, the method comprising:
  (a) hybridizing a primer bearing a first fluorophore to a segment of the target nucleic acid to form a labeled hybrid, wherein the 3'-end of the primer hybridizes to the target nucleic acid immediately adjacent to the variant site;
  (b) conducting template-dependent extension of the primer in the presence of a polymerase and at least one non-extendible nucleotide bearing a second fluorophore, whereby a double-labeled extension product is formed if the non-extendible nucleotide is complementary to the nucleotide at the variant site and the first and second fluorophore borne by the extension product are brought into an energy transfer relationship while the primer is hybridized to the target nucleic acid, and wherein the first and second fluorophore comprise a donor and an acceptor fluorophore which have a donor-acceptor spacing in the extension product of less than 18 nucleotides, the donor fluorophore having a high extinction coefficient and a low fluorescence quantum yield; and
  (c) detecting the presence or absence of the double-labeled extension product, the presence or absence of double-labeled extension product indicating the identity of the nucleotide at the variant site.

20. The method of claim 19, wherein the donor fluorophore is a cyanine dye.

21. The method of claim 20, wherein the cyanine dye is selected from the group consisting of CYA, Cy2, Cy3, Cy3.5, Cy5, Cy5.5, Cy7, and Cy7.5.

22. The method of claim 19, wherein the acceptor dye has a high quantum yield and a large extinction coefficient.

23. The method of claim 22, wherein the acceptor dye is selected from the group consisting of R110, R6G, TAMRA, ROX, FAM, JOE, ZOE, TET, HEX, NAN, Texas Red, and Rhodamine Red.

24. A method for analyzing variant sites in target nucleic acids, comprising:
  (a) conducting a plurality of template-dependent extension reactions with different primers, wherein different primers hybridize adjacent different variant sites on target nucleic acids, each extension reaction comprising
    (i) hybridizing one of the different primers to a segment of a target nucleic acid, wherein the primer bears a first fluorophore and an optional secondary label and the 3'-end of the primer hybridizes to a target nucleic acid immediately adjacent to a variant site,
    (ii) contacting the primer with a polymerase and at least one non-extendible nucleotide bearing a second fluorophore, whereby a multi-labeled extension product is formed if the non-extendible nucleotide is complementary to the nucleotide at the variant site and the first and second fluorophore borne by the extension product are brought into an energy transfer relationship while the primer is hybridized to the target nucleic acid; and wherein
      the first and second fluorophore comprise a donor and an acceptor fluorophore which have a donor-acceptor spacing in the extension product of less than 18 nucleotides; and
      different primers bear different first fluorophores and/or secondary labels and different non-extendible nucleotides optionally bear different second fluorophores such that different extension products corresponding to different variant sites bear different pairs of fluorophores and/or different secondary labels; and
  (b) detecting the presence or absence of the different extension products, the fluorophore pair and/or secondary label borne by the extension product indicating the identity of the nucleotides at the variant sites.

25. The method of claim 24, wherein the secondary label is attached to the 5'-end of the primer and is selected from the group consisting of a mass label, a radioisotope, a chromophore, a magnetic particle, an electron dense agent, and a metal chelate.

26. The method of claim 25, wherein the secondary label is a mass label.

27. The method of claim 24, wherein different primers bear different mass labels.

28. The method of claim 27, wherein the mass labels comprise one or more monomers and the different mass labels are composed of a different number of the monomers.

29. The method of claim 24, wherein the different variant sites are different sites on the same target nucleic acid or different sites on different target nucleic acids and the extension reactions are conducted in a single reaction vessel.

30. The method of claim 29, further comprising separating the different extension products prior to detecting the presence or absence of different extension products, separation being accomplished by HPLC or electrophoresis.

31. The method of claim 24, wherein the different variant sites are located on different target nucleic acids and each extension reaction is conducted in a separate reaction vessel, and further comprising collecting extension product from the reaction vessels prior to detection.

32. The method of claim 31, further comprising separating the different extension products prior to detecting the presence or absence of different extension products, separation being accomplished by HPLC or electrophoresis.

33. The method of claim 24, wherein the donor-acceptor spacing is 3–10 nucleotides.

34. The method of claim 24, wherein the donor-acceptor spacing is 4–6 nucleotides.

35. A method for determining the identity of a nucleotide at a site within a target nucleic acid, comprising:
  (a) hybridizing a primer containing a first fluorophore to a segment of said target nucleic acid to form a labeled hybrid, wherein the 3'-end of said primer hybridizes to said target nucleic acid adjacent to said site;
  (b) conducting template dependent extension of said primer with a polymerase by mixing a labeled non-extendible nucleotide linked to a second fluorophore and optionally one or more extendible nucleotides complementary to the nucleotide(s) of the target nucleic acid located between the primer 3' end and the variant site with said labeled hybrid under conditions appropriate for primer extension, whereby an energy-transfer (ET) labeled nucleic acid product is formed while the primer is hybridized to the target nucleic acid if said non-extendible nucleotide is complementary to the nucleotide at the site, and wherein said first and second fluorophore comprise a donor and an acceptor fluorophore which have a donor-acceptor spacing in the ET-labeled product of less than 18 nucleotides; and
  (c) detecting the presence or absence of ET-labeled product, the presence or absence of ET-labeled product indicating the identity of the nucleotide at the variant site.

36. The method according to claim 35, where the ET-labeled product is separated from the other components in the extension reaction followed by detection.

37. The method according to claim 35, where said separation is an electrophoretic separation.

38. The method according to claim 35, wherein the donor-acceptor spacing is from 4 to 6 nucleotides.

39. The method according to claim 38, wherein the donor-acceptor spacing is from 3 to 10 nucleotides.

40. The method according to claim 35, wherein said first fluorophore is a donor molecule and said second fluorophore is an acceptor molecule.

41. The method according to claim 35, wherein said first fluorophore is an acceptor molecule and said second fluorophore is a donor molecule.

42. A method for analyzing a variant site of a target nucleic acid, comprising:
  (a) hybridizing a primer bearing a first fluorophore to a segment of the target nucleic acid to form a labeled hybrid, wherein the 3'-end of the primer hybridizes to the target nucleic acid adjacent to the variant site;
  (b) conducting template-dependent extension of the primer in the presence of a polymerase and at least one dideoxynucleotide (ddNTP) bearing a second fluorophore, whereby a double-labeled extension product is formed if the non-extendible nucleotide is complementary to the nucleotide at the variant site and the first and second fluorophore borne by the extension product are brought into an energy transfer relationship during the extension reaction, wherein the first and second fluorophore comprise a donor and an acceptor fluorophore which have a donor-acceptor spacing in the extension product of less than 18 nucleotides;
  (c) separating any extension product formed from at least some of the unreacted primer and the unreacted dideoxynucleotide; and
  (d) detecting the presence or absence of one or both strands of the double-labeled extension product, the presence or absence of double-labeled extension product indicating the identity of the nucleotide at the variant site.

43. The method according to claim 42, wherein said conducting step is performed with a single dideoxynucleotide.

44. The method according to claim 42, wherein said conducting step comprises mixing said labeled hybrid with at least two ddNTPs.

45. The method according to claim 42, wherein said conducting step comprises mixing said labeled hybrid with at least two ddNTPs, each type of ddNTP bearing different labels.

46. The method according to claim 42, wherein said conducting step comprises mixing said labeled hybrid with ddATP, ddGTP, ddCTP and ddTTP.

47. A method for analyzing variant sites in target nucleic acids, comprising:
  (a) conducting a plurality of template-dependent extension reactions with different primers, wherein different primers hybridize adjacent different variant sites on target nucleic acids, each extension reaction comprising
    (i) hybridizing one of the different primers to a segment of a target nucleic acid, wherein the primer bears a first fluorophore and a secondary label and the 3'-end of the primer hybridizes to a target nucleic acid adjacent to a variant site,
    (ii) contacting the primer with a polymerase and at least one non-extendible nucleotide bearing a second fluorophore, whereby a multi-labeled extension product is formed if the non-extendible nucleotide is complementary to the nucleotide at the variant site and the first and second fluorophore borne by the extension product are brought into an energy transfer relationship, wherein the first and second fluorophore comprise a donor and an acceptor fluorophore which have a donor-acceptor spacing in the extension product of less than 18 nucleotides; and wherein different primers bear different secondary labels and different non-extendible nucleotides optionally bear different second fluorophores such that different extension products corresponding to different variant sites bear different secondary labels and optionally different second fluorophores; and
  (b) detecting the presence or absence of the different extension products, the secondary label and optionally the second fluorophore borne by the extension product indicating the identity the nucleotide at the variant site.

48. The method of claim 47, wherein the secondary label is a mass label such that different primers bear different mass labels and the method further comprises separating the different extension products according to size.

49. The method of claim 48, wherein
  each variant site is a biallelic site;
  each extension reaction is conducted with two labeled non-extendible nucleotides that are complementary to the two nucleotides potentially at the variant site and bear different second fluorophores; and
  the mass label and the second fluorophore borne by the extension product indicates the identity of the nucleotide at the variant site.

50. The method of claim 49, wherein the different extension products are separated on a single lane of an electrophoretic gel.

51. The method of claim 48, wherein
  each extension reaction is conducted with labeled non-extendible nucleotide analogs of dATP, dTTP, dCTP and dGTP that bear different second fluorophores; and
  the mass label and the second fluorophore borne by the extension product indicates the identity of the nucleotide at the variant site.

52. The method of claim 51, wherein the different extension products are separated on a single lane of an electrophoretic gel.

53. The method of claim 47, wherein the donor-acceptor spacing is 3–10 nucleotides.

54. The method of claim 47, wherein the donor-acceptor spacing is 4–6 nucleotides.

* * * * *